(12) United States Patent
Kruse et al.

(10) Patent No.: US 7,109,216 B2
(45) Date of Patent: Sep. 19, 2006

(54) 1H-IMIDAZOLE DERIVATIVES HAVING CB1 AGONISTIC, CB1 PARTIAL AGONISTIC OR CB1-ANTAGONISTIC ACTIVITY

(75) Inventors: Cornelis G. Kruse, Weesp (NL); Josephus H. M. Lange, Weesp (NL); Arnoldus H. J. Herremans, Weesp (NL); Herman H. van Stuivenberg, Weesp (NL)

(73) Assignee: Solvay Pharmaceuticals B.V. (NL)

( * ) Notice: Subject to any disclaimer, the term of this patent is extended or adjusted under 35 U.S.C. 154(b) by 0 days.

(21) Appl. No.: 10/912,171

(22) Filed: Aug. 6, 2004

(65) Prior Publication Data

US 2005/0054679 A1 Mar. 10, 2005

Related U.S. Application Data

(63) Continuation-in-part of application No. 10/490,019, filed as application No. PCT/EP02/10434 on Sep. 17, 2002.

(60) Provisional application No. 60/574,939, filed on May 28, 2004.

(30) Foreign Application Priority Data

Sep. 21, 2001 (EP) .................................. 01203851

(51) Int. Cl.
C07D 213/61 (2006.01)
A61K 31/4453 (2006.01)
(52) U.S. Cl. ...................... 514/318; 514/326; 546/193; 546/210
(58) Field of Classification Search ................. 546/210, 546/193; 514/318
See application file for complete search history.

(56) References Cited

U.S. PATENT DOCUMENTS

| | | | |
|---|---|---|---|
| 4,813,998 A | 3/1989 | Van Lommen et al. |
| 5,616,601 A | 4/1997 | Khanna et al. |
| 6,432,984 B1 | 8/2002 | Barth et al. |
| 6,518,264 B1 | 2/2003 | Achard et al. |
| 6,645,985 B1 | 11/2003 | Barth et al. |
| 6,858,603 B1 | 2/2005 | Achard et al. |
| 6,906,080 B1 | 6/2005 | Barth et al. |
| 6,960,601 B1 | 11/2005 | Smith et al. |
| 2004/0039024 A1 | 2/2004 | Barth et al. |
| 2004/0235816 A1 | 11/2004 | Achard et al. |
| 2004/0248956 A1 | 12/2004 | Hagmann et al. |
| 2005/0192332 A1 | 9/2005 | Barth et al. |

FOREIGN PATENT DOCUMENTS

| | | |
|---|---|---|
| FR | 2 783 246 A1 | 3/2000 |
| WO | WO 00/46209 A1 | 8/2000 |
| WO | WO 00/63204 A2 | 10/2000 |
| WO | WO 00/69848 A1 | 11/2000 |
| WO | WO 01/32663 A2 | 5/2001 |
| WO | WO 03/027076 A2 | 4/2003 |
| WO | WO 03/040107 A1 | 5/2003 |
| WO | WO 03/063781 A2 | 8/2003 |

OTHER PUBLICATIONS

Barth, F. et al., "Preparation and Formulation of Tricyclic Heterocycles Containing a Pyrazole-3-Carboxamide Subunit for Pharmaceutical Use as Cannanbinoid Receptor Antagonists," *Chem. Abstr.* 134, 340504 (2001).
Bodanszky, M et al., "The Practice of Peptide Synthesis," Springer-Verlag.; (ISBN: 0-387-57505-7) (2D ED. 1994).
Consroe, P., "Brain Cannabinoid Systems as Targets for the Therapy of Neurological Disorders," *Neurobiology of Disease* 5:534-551 (1998).
Dutta, A. et al., "Synthesis and Characterization of Novel Derivative of 2-Aminotetralins: Development of Highly Selective Derivatives for the D3 Receptor," *Med. Chem Res.* 10(4):208-229 (2000).
Dyck, B. et al., "Potent Imidazole and Triazole CB1 Receptor Antagonists Related to SR141716," *Bioorganic & Medicinal Chemistry Letters* 14:1151-1154 (2004).
Felder, C. et al., "LY320135, A Novel Cannabinoid CB1 Receptor Antagonist, Unmasks Coupling of the CB1 Receptor to Stimulation of cAMP Accumulation," *Journal of Pharmacology and Experimental Therapeutics* 284(1):291-297 (1998).

(Continued)

*Primary Examiner*—Kamal A. Saeed
*Assistant Examiner*—Nyeemah Grazier
(74) *Attorney, Agent, or Firm*—Finnegan, Henderson, Farabow, Garrett & Dunner, L.L.P.

(57) ABSTRACT

The present invention relates to a group of novel 1H-imidazole derivatives, to methods for the preparation of these compounds, and to pharmaceutical compositions containing one or more of these compounds as an active component.

These 1H-imidazole derivatives are potent cannabinoid-$CB_1$ receptor agonists, partial agonists or antagonists, useful for the treatment of psychiatric and neurological disorders, as well as and other diseases involving cannabinoid neurotransmission.

The compounds have the general formula (I)

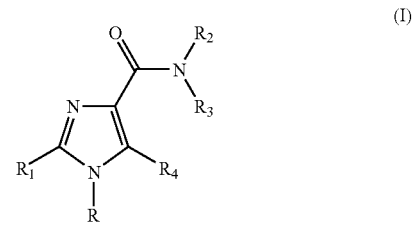

wherein R and $R_1$–$R_4$ have the meanings given in the specification.

13 Claims, No Drawings

OTHER PUBLICATIONS

Goya, P. et al., "Recent Advances in Cannabinoid Receptor Agonists and Antagonists," *Exp. Opin. Ther. Patents* 10(10):1529-1538 (2000).

Greenberg, D., "Cannabinoids and Neuroprotection in Stroke," *Drug News Perspect* 12(8):458-462 (1999).

Guillemet, M. et al., "A Simple Synthesis of New Push-Pull Substituted Imidazoles by Chemoselective Nucleophilic Attack of α-Cyano Epoxides," *Tetrahedron Letters*, 36(4):547-548 (1995).

Hosohata, K. et al., "AM630 Is a Competitive Cannabinoid Receptor Antagonist in the Guinea Pig Brain," *Life Sciences*, 61(9):115-118 (1997).

Kanyonyo, M. et al., "3-Alkyl-(5,5'-Diphenyl)Imidazolidinediones As New Cannabinoid Receptor Ligands," *Bioorganic & Medicinal Chemistry Letters* 9:2233-2236 (1999).

Khanna, I. et al., "1,2-Diarylimidazoles as Potent, Cyclooxygenase-2 Selective, and Orally Active Anti-inflammatory Agents," *J. Med. Chem.* 40:1634-1647 (1997).

Khanna, I. et al., "Selective Cyclooxygenase-2 Inhibitors: Heteroaryl Modified 1,2-Diarylimidazoles Are Potent, Orally Active Antiinflammatory Agents," *J. Med. Chem.* 43:3168-3185 (2000).

King, F.D., Ed., Medicinal Chemistry: Principles and Practice, p. 215 (1994), ISBN: 0-85186-494-5.

Kudo, N. et al., "Synthesis and Herbicidal Activity of 1,5-Diarylpyrazole Derivatives," *Chem. Pharm. Bull.* 47(6):857-868 (1999).

Lan, R. et al., "Structure—Activity Relationships of Pyrazole Derivatives as Cannabinoid Receptor Antagonists," *J. Med. Chem.* 42:769-776 (1999).

Landsman, R. et al., "SR141716A is an Inverse Agonist at the Human Cannabinoid $CB_1$ Receptor," *European Journal of Pharmacology* 344:R1-R2 (1997).

Li, Z. et al., "Facile Synthesis of Amidines Via Intermolecular Reductive Coupling of Nitriles with Azobenzene Promoted by Samarium Diiodide", *Chemical Abstracts* 133(18):1 (2000).

Matsuda, L. et al., "Cannabinoid Receptors: Which Cells, Where, How, and Why?," NIDA Research Monograph, 48-56 (T. Lee, Ed.) (1992).

Matsuda, L. et al., "Molecular Biology of the Cannabinoid Receptor," *Academic Press*, 117-140, (R. Pertwee, Ed.) (1995).

Matthews, W. et al., "Synthesis of [$^{18}$F] SR144385: A Selective Radioligand for Positron Emission Tomographic Studies of Brain Cannabinoid Receptors," *J. Labelled Cpd. Radiopharm.* 42:589-596 (1999).

Mechoulam, R. et al., "Endocannabinoids," *Eur. J. Pharmacol.* 359:1-18 (1998).

Mechoulam, R. et al., "Towards Cannabinoid Drugs—Revisited," *J. Prog. Med. Chem.* 35:199-243 (1998).

Mechoulam, R. et al., "Towards Cannabinoid Drugs," *J. Prog. Med. Chem.* 24:159-207 (1987).

Meschler, J. et al., "Inverse Agonist Properties of N-(Piperidin-1-yl)-5-(4-chlorophenyl)-1-(2,4-dichlorophenyl)-4-methyl-1H-pyrazole-3-carboxamide HCl (SR141716A) and 1-(2-Chlorophenyl)-4-cyano-5-(4-methoxyphenyl)-1H-pyrazole-3-carboxylic Acid Phenylamide (CP-272871) for the $CB_1$ Cannabinoid Receptor," *Biochem. Pharmacol.* 60:1315-1323 (2000).

Mignani, S. et al., "Preparation of 1-Bis(aryl)methyl-3-(alkylsulfonyl)arylmethyleneazetidines as Cannabinoid $CB_1$ Receptor Antagonists," *Chemical Abstracts* 132(18):699 (2000).

Munro, S. et al., "Molecular Characterization of a Peripheral Receptor for Cannabinoids," *Nature* 365:61-65 (1993).

Nakamura-Palacios, E. et al., "The Pharmacology of SR 141716A: A Review," *CNS Drug Review* 5(1):43-58 (1999).

Pertwee, R., "Cannabinoid Receptors and Pain," *Progress in Neurobiology* 63:569-611 (2001).

Pertwee, R., "Neuropharmacology and Therapeutic Potential of Cannabinoids," *Addiction Biology* 5:37-46 (2000).

Pertwee, R., "Pharmacology of Cannabinoid Receptor Ligands," *Current Medicinal Chemistry* 6:635-664 (1999).

Pertwee, R., "Cannabinoids and the Gastrointestinal Tract," *Gut* 48:859-867 (2001).

Pop, E., "Developing Cannabinoids as Potential Central Nervous System Agents," *Current Opinion in CPNS Investigational Drugs* 1(5):587-596 (1999).

Robson, P., "Therapeutic Aspects of Cannabis and Cannabinoids," *Journal of Psychiatry* 178:107-115 (2001).

Seifert, P. et al., "Einige Reaktionen and Derivaten von α-Ketosäuren und α-Ketosäureestern," *Helv. Chim. Acts* 33(99):725-736 (1950).

Smith, M. et al., "Crown Ether Complexes and Cryptates," *Advanced Organic Chemistry*, 5th Ed., pp. 105-109 (2001), John Wiley & Sons, New York, ISBN: 0471-585890.

Smith, M. et al., Advanced Organic Chemistry, 5th Ed., pp. 215-217 (2001), John Wiley & Sons, New York, ISBN: 0471-585890.

Stella, V., "Prodrugs as Therapeutics," Expert Opin. Ther. Patents, 14(3):277-280 (2004).

Thomas, B. F. et al., "Comparative Receptor Binding Analyses of Cannabinoid Agonists and Antagonists," *Journal of Pharmacology and Experimental Therapeutics* 285(1):285-292 (1998).

Tsuji, K. et al., "Studies on Anti-inflammatory Agents. IV.[1)] Synthesis and Pharmacological Properties of 1,5-Diarylpyrazoles and Related Derivatives," *Chem. Pharm. Bull.* 45(6):987-995 (1997).

Ueda, T. et al., "A Novel Ring Transformation of 5-Acylaminouracils and 5-Acylamino-Pyrimidin-4(3H)-Ones into Imidazoles," *Tetrahedron Letters* 29(36):4607-4610 (1988).

Wiley, J. et al., "Novel Pyrazole Cannabinoids: Insights into $CB_1$ Receptor Recognition and Activation," *J. Pharmacol. Exp. Ther.* 296(3):1013-1022 (2001).

Williamson, E. et al. "Cannabinoids in Clinical Practice," *Drugs* 60(6):1303-1314 (2000).

1H-IMIDAZOLE DERIVATIVES HAVING CB1 AGONISTIC, CB1 PARTIAL AGONISTIC OR CB1-ANTAGONISTIC ACTIVITY

This application is a continuation-in-part and claims benefit of priority under 35 U.S.C. § 120 of U.S. application Ser. No. 10/490,019, which is a § 371 of PCT Application No. PCT/EP02/10434, filed on Sep. 17, 2002, and claims benefit of priority under 35 U.S.C. § 119 of European Patent Application No. 01203851.9, filed on Sep. 21, 2001. Applicants also claim benefit of priority under 35 U.S.C. § 119(e) of U.S. Provisional Application No. 60/574,939, filed on May 28, 2004. Each of the foregoing applications is incorporated herein by reference.

The present invention relates to a group of novel 1H-imidazole derivatives, to methods for the preparation of these compounds, and to pharmaceutical compositions containing one or more of these compounds as an active component.

These 1H-imidazole derivatives are potent cannabinoid-$CB_1$ receptor agonists, partial agonists or antagonists, useful for the treatment of psychiatric and neurological disorders, as well as and other diseases involving cannabinoid neurotransmission.

Cannabinoids are present in the Indian hemp *Cannabis sativa* and have been used as medicinal agents for centuries (Mechoulam, R. and Feigenbaum, J. J. *Prog. Med. Chem.* 1987, 24, 159). However, only within the past ten years the research in the cannabinoid area has revealed pivotal information on cannabinoid receptors and their (endogenous) agonists and antagonists. The discovery and the subsequent cloning of two different subtypes of cannabinoid receptors ($CB_1$ and $CB_2$) stimulated the search for novel cannabinoid receptor antagonists (Munro, S. et al., *Nature* 1993, 365, 61. Matsuda, L. A. and Bonner, T. I. *Cannabinoid Receptors*, Pertwee, R. G. Ed. 1995, 117, Academic Press, London). In addition, pharmaceutical companies became interested in the development of cannabinoid drugs for the treatment of diseases connected with disorders of the cannabinoid system (Consroe, P. *Neurobiology of Disease* 1998, 5, 534. Pop, E. *Curr. Opin. In CPNS Investigational Drugs* 1999, 1, 587. Greenberg, D. A. *Drug News Perspect.* 1999, 12, 458. Pertwee, R. G., *Progress in Neurobiology* 2001, 63, 569). Hitherto, several $CB_1$ receptor antagonists are known. Sanofi disclosed their diarylpyrazole congeners as selective $CB_1$ receptor antagonists. A representative example is SR-141716A (Dutta, A. K. et al., *Med. Chem. Res.* 1994, 5, 54. Lan, R. et al., *J. Med. Chem.* 1999, 42, 769. Nakamura-Palacios, E. M. et al., *CNS Drug Rev.* 1999, 5, 43). CP-272871 is a pyrazole derivative, like SR141716A, but less potent and less $CB_1$ receptor subtype-selective than SR141716A (Meschler, J. P. et al., *Biochem. Pharmacol.* 2000, 60, 1315). Aminoalkylindoles have been dis-closed as $CB_1$ receptor antagonists. A representative example is Iodopravadoline (AM-630), which was introduced in 1995. AM-630 is a moderately active $CB_1$ receptor antagonist, in some assays behaving as a weak partial agonist (Hosohata, K. et al., *Life Sc.* 1997, 61, PL115). Researchers from Eli Lilly described aryl-aroyl substituted benzofurans as selective $CB_1$ receptor antagonists (e.g. LY-320135) (Felder, C. C. et al., *J. Pharmacol. Exp. Ther.* 1998, 284, 291). 3-Alkyl-5,5'-diphenylimidazolidine-diones were described as cannabinoid receptor ligands, which were indicated to be cannabinoid antagonists (Kanyonyo, M. et al., *Biorg. Med. Chem. Lett.* 1999, 9, 2233). Aventis Pharma claimed diarylmethyleneazetidine analogs as $CB_1$ receptor antagonists (Mignani, S. et al., Patent FR 2783246, 2000; *Chem. Abstr.* 2000, 132, 236982). Tricyclic pyrazoles were claimed by Sanofi-Synthelabo as $CB_1$ antagonists (Barth, F. et al. Patent WO 0132663, 2001; *Chem. Abstr.* 2001, 134, 340504). Interestingly, many $CB_1$ receptor antagonists have been reported to behave as inverse agonists in vitro (Landsman, R. S. et al., *Eur. J. Pharmacol.* 1997, 334, R1). Pyrazole cannabinoids have also been reported as $CB_1$ receptor partial agonists showing in vivo cannabimimetic effects (Wiley, J. L. et al., *J. Pharmacol. Exp. Ther.* 2001, 296, 1013). A number of classes of $CB_1$ receptor agonists are known such as for example the classical cannabinoids (e.g. $\Delta^9$-THC), non-classical cannabinoids, aminoalkylindoles and eicosanoids (e.g. anandamide). Reviews provide a nice overview of the cannabinoid research area (Mechoulam, R. et al., *Prog. Med. Chem.* 1998, 35, 199. Lambert, D. M. *Curr. Med. Chem.* 1999, 6, 635. Mechoulam, R. et al., *Eur. J. Pharmacol.* 1998, 359, 1. Williamson, E. M. and Evans, F. J. *Drugs* 2000, 60, 1303. Pertwee, R. G. *Addiction Biology* 2000, 5, 37. Robson, P. *Br. J. Psychiatry* 2001, 178, 107. Pertwee, R. G. *Prog. Neurobiol.* 2001, 63, 569. Goya, P. and Jagerovic, N. *Exp. Opin. Ther. Patents* 2000, 10, 1529. Pertwee, R. G. *Gut* 2001, 48, 859).

It has now surprisingly been found that the novel 1H-imidazole derivatives of the formula (I), prodrugs thereof, and salts thereof, are potent agonists, partial agonists, or antagonists on cannabinoid-$CB_1$ receptors:

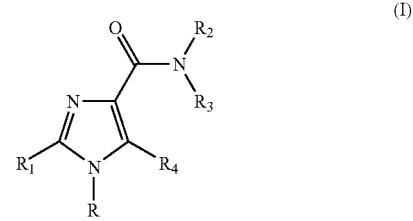

(I)

wherein

R represents phenyl, thienyl, 2-pyridinyl, 3-pyridinyl, 4-pyridinyl, pyrimidinyl, pyrazinyl, pyridazinyl or triazinyl, which groups may be substituted with 1, 2, 3 or 4 substituents Y, which can be the same or different, from the group $C_{1-3}$-alkyl or alkoxy, hydroxy, halogen, trifluoromethyl, trifluoromethylthio, trifluoromethoxy, nitro, amino, mono- or dialkyl $(C_{1-2})$-amino, mono- or dialkyl $(C_{1-2})$-amido, $(C_{1-3})$-alkoxycarbonyl, carboxyl, cyano, carbamoyl and acetyl, or R represents naphtyl, with the proviso that when R is 4-pyridinyl, $R_4$ represents a halogen atom or a cyano, carbamoyl, formyl, acetyl, trifluoroacetyl, fluoroacetyl, propionyl, sulfamoyl, methanesulfonyl, methylsulfanyl or branched or unbranched $C_{1-4}$ alkyl group, which $C_{1-4}$ alkyl group may be substituted with 1–3 fluoro atoms or with a bromo, chloro, iodo, cyano or hydroxy group, $R_1$ represents phenyl or pyridinyl, which groups may be substituted with 1–4 substituents Y, which can be the same or different, wherein Y has the above mentioned meaning, or $R_1$ represents pyrimidinyl, pyrazinyl, pyridazinyl or triazinyl, which groups may be substituted with 1–2 substituents Y, which can be the same or different or $R_1$ represents a five-membered aromatic heterocyclic ring having one or two heteroatoms from the group (N, O, S), which heteroatoms can be the same or different, which five-membered aromatic heterocyclic ring may be substituted with 1–2 substituents Y, which can be the same or different or $R_1$ represents naphtyl, $R_2$ represents H, branched or unbranched $C_{1-8}$ alkyl, $C_{3-8}$ cycloalkyl, $C_{3-8}$ alkenyl, $C_{5-8}$ cycloalkenyl which groups may contain a sulfur, oxygen or nitrogen atom, $R_3$ represents branched or unbranched $C_{2-8}$ alkyl, $C_{1-8}$ alkoxy, $C_{5-8}$ cycloalkyloxy, $C_{3-8}$ cycloalkyl, $C_{5-10}$ bicycloalkyl, $C_{6-10}$ tricycloalkyl, $C_{3-8}$ alkenyl, $C_{5-8}$ cycloalkenyl, which groups may optionally contain one or more heteroatoms from the group (O, N, S) and which groups may be substituted with a hydroxy group or 1–2 $C_{1-3}$ alkyl groups or 1–3 fluoro atoms, or $R_3$ represents a benzyl or phenethyl group which aromatic rings may be substituted with 1–5 substituents Z, which can be the same or different, from the group $C_{1-3}$-alkyl or alkoxy, hydroxy, halogen, trifluoromethyl, trifluoromethylthio, trifluoromethoxy, nitro, amino, mono- or dialkyl $(C_{1-2})$-amino, mono- or dialkyl $(C_{1-2})$-amido, $(C_{1-3})$-alkylsulfonyl, dimethyl-sulfamido, $C_{1-3}$-alkoxycarbonyl, carboxyl, trifluoromethylsulfonyl, cyano, carbamoyl, sulfamoyl and acetyl, or $R_3$ represents a phenyl or pyridinyl group, which groups are substituted with 1–4 substituents Z, wherein Z has the meaning as indicated above, or $R_3$ represents a pyridinyl group, or $R_3$ represents a phenyl group, with the proviso that $R_4$ represents a halogen atom or a cyano, carbamoyl, formyl, acetyl, trifluoroacetyl, fluoroacetyl, propionyl, sulfamoyl, methanesulfonyl, methylsulfanyl or $C_{1-4}$ alkyl group, which $C_{1-4}$ alkyl group may be substituted with 1–3 fluoro atoms or with a bromo, chloro, iodo, cyano or hydroxy group, or $R_3$ represents a group $NR_5R_6$, with the proviso that $R_2$ represents a hydrogen atom or a methyl group, wherein $R_5$ and $R_6$ are the same or different and represent branched or unbranched $C_{1-4}$ alkyl, or $R_5$ and $R_6$—together with the nitrogen atom to which they are bonded—form a saturated or unsaturated, monocyclic or bicyclic heterocyclic group having 4 to 10 ring atoms which heterocyclic group contains one or two heteroatoms from the group (N, O, S), which heteroatoms can be the same or different, which heterocyclic group may be substituted with a $C_{1-3}$ alkyl group or a hydroxy group, or $R_2$ and $R_3$—together with the nitrogen atom to which they are bonded—form a saturated or unsaturated heterocyclic group having 4 to 10 ring atoms which heterocyclic group contains one or two heteroatoms from the group (N, O, S), which heteroatoms can be the same or different, which heterocyclic group may be substituted with a $C_{1-3}$ alkyl group or a hydroxy group, $R_4$ represents a hydrogen or halogen atom or a cyano, carbamoyl, formyl, acetyl, trifluoroacetyl, fluoroacetyl, propionyl, sulfamoyl, methanesulfonyl, methylsulfanyl or branched or unbranched $C_{1-4}$ alkyl group, which $C_{1-4}$ alkyl group may be substituted with 1–3 fluoro atoms or with a bromo, chloro, iodo, cyano or a hydroxy group.

Due to the potent $CB_1$ agonistic, partial agonistic or antagonistic activity the compounds according to the invention are suitable for use in the treatment of psychiatric disorders such as psychosis, anxiety, depression, attention deficits, memory disorders, cognitive disorders, appetite disorders, obesity, addiction, appetence, drug dependence and neurological disorders such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, diabetes, cancer, emesis, nausea, gastrointestinal disorders, gastric ulcers, diarrhoea and cardiovascular disorders.

The affinity of the compounds of the invention for cannabinoid $CB_1$ receptors was determined as described below (see Table 1). From the binding affinity measured for a given compound of formula I, one can estimate a theoretical lowest effective dose. At a concentration of the compound equal to twice the measured $K_i$, 100% of the $CB_1$ receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value.

Other embodiments of the present invention include the compounds of formula (I) in which:

R represents phenyl, thienyl, 2-pyridinyl, or 3-pyridinyl, which groups may be substituted with 1, 2, 3 or 4 substituents Y, which can be the same or different, from the group $C_{1-3}$-alkyl or alkoxy, hydroxy, halogen, trifluoromethyl, trifluoromethylthio, trifluoromethoxy, nitro, amino, mono- or dialkyl $(C_{1-2})$-amino, mono- or dialkyl $(C_{1-2})$-amido, $(C_{1-3})$-alkoxycarbonyl, carboxyl, cyano, carbamoyl and acetyl, or R represents naphthyl, or R represents 4-pyridinyl, with the proviso that $R_4$ represents halogen or $C_{1-4}$ alkyl group, which $C_{1-4}$ alkyl group may be substituted with a fluoro atom or a hydroxy group, $R_1$ represents phenyl, thienyl or pyridinyl, which groups may be substituted with 1–4 substituents Y, which can be the same or different, or $R_1$ represents naphtyl, $R_2$ represents H, $C_{1-8}$ alkyl, $C_{3-8}$ cycloalkyl, $C_{3-8}$ alkenyl, $C_{5-8}$ cycloalkenyl which groups may contain a sulfur, oxygen or nitrogen atom, $R_3$ represents $C_{2-8}$ alkyl, $C_{1-8}$ alkoxy, $C_{3-8}$ cycloalkyl, $C_{5-10}$ bicycloalkyl, $C_{6-10}$ tricycloalkyl, $C_{3-8}$ alkenyl, $C_{5-8}$ cycloalkenyl, which groups may optionally contain one or more atoms from the group (O, N, S), or $R_3$ represents a benzyl or phenethyl group, which aromatic rings thereof may be substituted with 1–5 substituents Z, which can be the same or different, from the group $C_{1-3}$-alkyl or alkoxy, hydroxy, halogen, trifluoromethyl, trifluoromethylthio, trifluoromethoxy, nitro, amino, mono- or dialkyl $(C_{1-2})$-amino, mono- or dialkyl $(C_{1-2})$-amido, $(C_{1-3})$-alkylsulfonyl, dimethylsulfamido, $C_{1-3}$-alkoxycarbonyl, carboxyl, trifluoromethylsulfonyl, cyano, carbamoyl, sulfamoyl and acetyl, or $R_3$ represents a phenyl group substituted with 1–5 substituents Z, wherein Z has the meaning as indicated above, or $R_3$ represents a group $NR_5R_6$ with the proviso that $R_2$ represents a hydrogen atom or a methyl group, wherein $R_5$ and $R_6$ are the same or different and represent $C_{1-4}$ alkyl, or $R_5$ and $R_6$—together with the nitrogen atom to which they are bonded—form a saturated or unsaturated heterocyclic moiety having 4 to 10 ring atoms, which heterocyclic moiety may be substituted with a $C_{1-3}$ alkyl group or a hydroxy group, or R$_2$ and R$_3$—together with the nitrogen atom to which they are bonded—form a saturated or unsaturated heterocyclic moiety having 4 to 10 ring atoms, which heterocyclic moiety may be substituted with a C$_{1-3}$ alkyl group or a hydroxy group, R$_4$ represents hydrogen, halogen or a C$_{1-4}$ alkyl group, which C$_{1-4}$ alkyl group may be substituted with a fluoro atom or a hydroxy group.

Further embodiments of the present invention include the compounds of formula (I) in which:

R represents phenyl, which may be substituted with a substituent chosen from F, Cl, Br, Me, OMe, and CF$_3$, R$_1$ represents phenyl, which may be substituted with one or two substituents, which are the same or different, chosen from F, Cl, Br, Me, OMe, and CF$_3$, R$_2$ represents H, lower alkyl, alkylamino, alkoxy, benzyl, cycloalkyl, pipyridinyl, pyrrolidinyl, tert-butoxy, or phenyl, R$_3$ represents H, lower alkyl, alkylamino, alkoxy, benzyl, cycloalkyl, pipyridinyl, pyrrolidinyl, tert-butoxy, or phenyl, and R$_4$ represents H, Me, or ethyl.

The invention relates both to racemates, mixtures of diastereomers and the individual stereoisomers of the compounds having formula (I).

The present invention also relates to prodrugs of the compounds of formula (I). Prodrugs are bioreversible derivatives of drug molecules used to overcome some barriers to the utility of the parent drug molecule. These barriers include, but are not limited to, solubility, permeability, stability, presystemic metabolism and targeting limitations (J. Stella, "Prodrugs as therapeutics", Expert Opin. Ther. Patents, 14(3), 277–280, 2004). Pro-drugs, i.e., compounds which when administered to humans by any known route, are metabolized to compounds having formula (I), belong to the invention. For example, this includes compounds with primary or secondary amino or hydroxy groups. Such compounds can be reacted with organic acids to yield compounds having formula (I) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone. A pro-drug is an inactive compound, which when administered is converted into an active form. See Medicinal Chemistry: Principles and Practice, 1994, ISBN 0-85186-494-5, Ed.: F. D. King, p. 215.

The compounds of the invention can be brought into forms suitable for administration by means of usual processes using auxiliary substances such as liquid or solid carrier materials. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

The dosage administered can range across 0.001–1000 mg/kg, 0.01–500 mg/kg, or 0.1–100 mg/kg of patient's bodyweight.

Suitable synthetic routes for the compounds of the invention are the following:

Synthetic Route A

Step 1: ester hydrolysis of a compound having formula (II) wherein R$_7$ represents a branched or unbranched alkyl group (C$_{1-4}$) or benzyl group

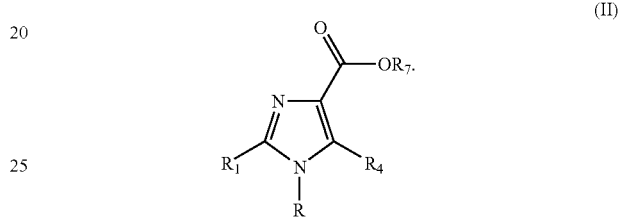

(II)

This reaction gives a compound having formula (III)

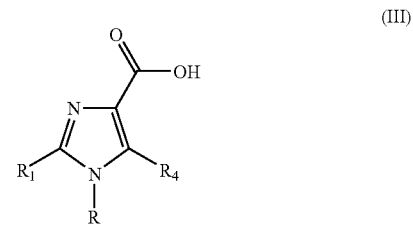

(III)

wherein R, R$_1$ and R$_4$ have the meanings as described above.

Intermediates having formula (II), wherein R$_7$ represents a branched or unbranched alkyl group (C$_{1-4}$) or benzyl group can be obtained according to methods known, for example:

a) I. K. Khanna et al., *J. Med. Chem.* 2000, 43, 3168–3185 b) N. Kudo et al., *Chem. Pharm. Bull.* 1999, 47, 857–868 c) K. Tsuji et al., *Chem. Pharm. Bull.* 1997, 45, 987–995 d) I. K. Khanna et al., *J. Med. Chem.* 1997, 40, 1634–1647 e) M. Guillemet et al., *Tetrahedron Lett.* 1995, 36, 547–548

Step 2: reaction of a compound having formula (III) with a compound having formula R$_2$R$_3$NH wherein R$_2$ and R$_3$ have the meanings as described above via activating and coupling methods such as formation of an active ester, or in the presence of a coupling reagent such as DCC, HBTU, BOP or similar reagents. This reaction gives a desired 1H-imidazole derivative having formula (I). (For more information on activating and coupling methods see: M. Bodanszky and A. Bodanszky: *The Practice of Peptide Synthesis*, Springer-Verlag, New York, 1994; ISBN: 0-387-57505-7).

Alternatively, a compound having formula (III) is reacted with a halogenating agent, for example thionyl chloride (SOCl$_2$). This reaction gives the corresponding carbonyl chloride (IV).

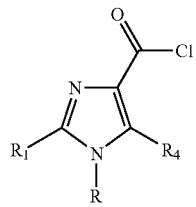

(IV)

Reaction of a compound having formula (IV) with a compound having formula R$_2$R$_3$NH wherein R$_2$ and R$_3$ have the meanings as described above, yields a 1H-imidazole derivative having formula (I). This reaction is preferably carried out in the presence of an organic base such as for example diisopropylethylamine (DIPEA) or triethylamine.

Alternatively, a compound having formula (II) is reacted in an amidation reaction with a compound having formula R$_2$R$_3$NH wherein R$_2$ and R$_3$ have the meanings as described above to give a 1H-imidazole derivative having formula (I).

Synthetic Route B

Reaction of a compound having formula (II), wherein R$_4$ represents hydrogen and wherein R, R$_1$ and R$_7$ have the meanings as described above for compound (II), with a compound having general formula R$_4$'—X, wherein X represents a leaving group and R$_4$' represents a C$_{1-4}$ alkyl group, which alkyl group may be substituted with 1–3 fluoro atoms or wherein R$_4$' represents a cyano, formyl, acetyl, trifluoroacetyl, fluoroacetyl, methylsulfanyl or propionyl moiety, or a halogen atom. This reaction is carried out in the presence of a strong non-nucleophilic base such as lithium diisopropylamide (LDA), preferably under anhydrous conditions in an inert organic solvent, for example tetrahydrofuran, and yields a compound having formula (II)

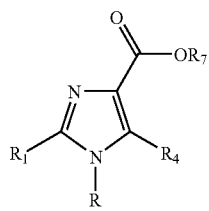

(II)

wherein R, R$_1$ and R$_7$ have the meanings as described hereinabove and R$_4$ represents a C$_{1-4}$ alkyl group, which alkyl group may be substituted with 1–3 fluoro atoms or wherein R$_4$ represents a cyano, formyl, acetyl, trifluoroacetyl, fluoroacetyl, methylsulfanyl or propionyl group, or a halogen atom.

Compounds of general formula (II) which have been obtained according to synthesis route B can be converted to compounds of general formula (I) analogously to the procedures described in synthesis route A, step 1 of route A or step 2 of route A (see above).

Synthetic Route C

Compounds having formula (II)

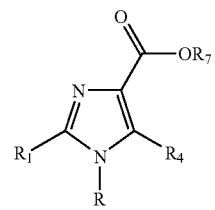

(II)

wherein R$_4$ represents a branched or unbranched C$_{1-4}$ alkyl group, which C$_{1-4}$ alkyl group may be substituted with 1–3 fluoro substituents and wherein R, R$_1$ have the meanings given above and R$_7$ represents a branched or unbranched alkyl group (C$_{1-4}$) or benzyl group can be synthesized by reacting a compound having formula (V) or its tautomer

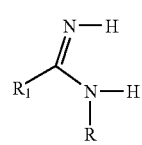

(V)

wherein R and R$_1$ have the meanings given above, with a compound having formula (VI)

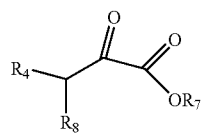

(VI)

wherein R$_4$ represents a branched or unbranched C$_{1-4}$ alkyl group, which C$_{1-4}$ alkyl group may be substituted with 1–3 fluoro atoms and R$_8$ represents a leaving group, for example a bromo substituent, and R$_7$ represents a branched or unbranched alkyl group (C$_{1-4}$) or benzyl group. The reaction is preferably carried out in an organic solvent, for example in 2-propanol or in N-methyl-2-pyrrolidinone (NMP). The addition of an acid like trifluoroacetic acid (TFA) during the reaction may enhance the formation of the compounds having formula (II). (For more information on the leaving group concept see: M. B. Smith and J. March: *Advanced organic chemistry*, p. 275, 5$^{th}$ ed., (2001) John Wiley & Sons, New York, ISBN: 0-471-58589-0).

Compounds of general formula (II) which have been obtained according to synthesis route C can be converted to compounds of general formula (I) analogously to the procedures described in synthesis route A, step 1 of route A or step 2 of route A (see above).

Compounds of the invention having formula (VI) can be obtained according to methods known, for example: P. Seifert et al., *Helv. Chim. Acta*, 1950, 33, 725.

Synthetic Route D
Reaction of a compound having formula (II)

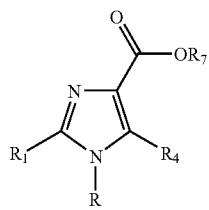

(II)

wherein R₄ represents a methyl group and R, R₁ have the meanings given above and R₇ represents a branched or unbranched alkyl group (C₁₋₄) or benzyl group with a regioselective brominating compound such as N-bromosuccinimide (NBS) in an organic solvent such as CCl₄ in the presence of a free-radical initiator like dibenzoyl peroxide gives a compound of formula (VII)

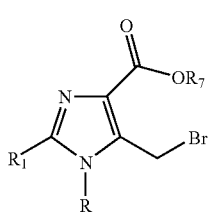

(VII)

wherein R, R₁ and R₇ have the meanings given above. Reaction of a compound having formula (VII) (analogous to the method described in Mathews, W. B. et al., *J. Label. Compds. Radiopharm.*, 1999, 42, 589) with for example KCl, KI, KF or KCN gives a compound of formula (VIII)

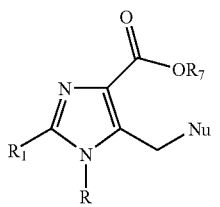

(VIII)

wherein R, R₁ and R₇ have the meanings given hereinabove and Nu represents a chloro, iodo, fluoro or cyano group. The reaction is preferably carried out in the presence of a weak base like NaHCO₃ or in the presence of a crown ether or a cryptand. (For more information on crown ethers and cryptands see: M. B. Smith and J. March: *Advanced organic chemistry*, p. 105, 5ᵗʰ ed., (2001) John Wiley & Sons, New York, ISBN: 0-471-58589-0).

Compounds of general formula (VII) or (VIII) which have been obtained according to synthesis route D can be converted to compounds of general formula (I) analogously to the procedures described in synthesis route A, step 1 of route A, or step 2 of route A (see above).

Experimental: Chemistry
¹H and ¹³C NMR spectra were recorded on a Bruker Avance DRX600 instrument (600 MHz), Varian UN400 instrument (400 MHz) or on a Varian VXR200 instrument (200 MHz) using DMSO-d₆ or CDCl₃ as solvents with tetramethylsilane as an internal standard. Chemical shifts are given in ppm (δ scale) downfield from tetramethylsilane. Coupling constants (J) are expressed in Hz. Flash chromatography was performed using silica gel 60 (0.040–0.063 mm, Merck). Column chromatography was performed using silica gel 60 (0.063–0.200 mm, Merck). Melting points were recorded on a Büchi B-545 melting point apparatus. Mass spectra were recorded on a Micromass QTOF-2 instrument with MassLynx application software for acquisition and reconstruction of the data. Exact mass measurement was done of the quasimolecular ion [M+H]⁺.

EXAMPLE 1

Part A: To a 1M solution of sodium bis(trimethylsilyl)amide in THF (70 mL) is added dropwise a solution of 4-chloroaniline (8.86 gram, 69.5 mmol) in anhydrous THF in a nitrogen atmosphere. After the mixture is stirred for 20 minutes a solution of 2,4-dichlorobenzonitrile (12 gram, 70 mmol) in THF is added. The resulting mixture is stirred overnight, poured into ice-water (400 mL) and extracted with dichloromethane, dried over Na₂SO₄ and concentrated in vacuo to give a yellow oil (15.7 gram). Crystallisation from a dichloromethane/heptane mixture, and subsequent washing with methyl-t-butyl ether gives N-(4-chlorophenyl)-2,4-dichlorobenzenecarboxamidine (8.66 gram, 42% yield) as a yellow solid. Melting point (MP): 93–95° C.
Analogously was prepared:
N-(4-bromophenyl)-2,4-dichlorobenzenecarboxamidine. MP: 117–119° C.

Part B: A mixture of N-(4-chlorophenyl)-2,4-dichlorobenzenecarboxamidine (2.00 gram, 6.68 mmol), ethyl 3-bromo-2-oxopropanoate (2.65 gram, 13.6 mmol) and NaHCO₃ (1.12 gram, 13.3 mmol) in 2-propanol is stirred at reflux temperature for 20 hours. After cooling to room temperature the mixture is concentrated in vacuo and the residue suspended in dichloromethane, washed with water (3×50 mL) and brine (3×50 mL). The aqueous layers are extracted with dichloromethane. The combined organic layers are dried over Na₂SO₄ and concentrated in vacuo to afford crude brown product (2.0 gram). This product is further purified by column chromatography (silicagel, heptane/EtOAc=90/10 (v/v)) to yield ethyl 1-(4-chlorophenyl)-2-(2,4-dichlorophenyl)-1H-imidazole-4-carboxylate (0.759 gram, 29% yield) as a yellow oil which slowly solidifies on standing. Melting point: 150–152° C.; MS: 395 (MH⁺). ¹H-NMR (400 MHz, CDCl₃): δ 7.91 (s, 1H), 7.49 (dd, J=8 Hz, J=2 Hz, 1H), 7.29–7.36 (m, 4H), 7.07 (dt, J=8 Hz, J=2 Hz, 2H), 4.44 (q, J=7 Hz, 2H), 1.42 (t, J=7 Hz, 3H).

Part C: Ethyl 1-(4-chlorophenyl)-2-(2,4-dichlorophenyl)-1H-imidazole-4-carboxylate (0.810 gram, 2.06 mmol) and LiOH (0.173 g, 7.20 mmol) are dissolved in a H₂O/THF (20 mL/20 mL) mixture and stirred at 50° C. for 16 hours. The mixture is concentrated in vacuo to give 1-(4-chlorophenyl)-2-(2,4-dichlorophenyl)-1H-imidazole-4-carboxylic acid. Thionyl chloride (60 mL) is added and the mixture is heated at reflux temperature for 1 hour and concentrated in vacuo to give crude 1-(4-chlorophenyl)-2-(2,4-dichlorophenyl)-1H-imidazole-4-carbonyl chloride.

Part D: Crude 1-(4-chlorophenyl)-2-(2,4-dichlorophenyl)-1H-imidazole-4-carbonyl chloride (919 mg, ~2.39 mmol), 1-aminopiperidine (0.469 g, 4.69 mmol) and triethylamine (0.363 g, 3.59 mmol) are dissolved in dichloromethane and stirred for one hour at room temperature. The mixture is washed with a saturated aqueous NaHCO₃ solution (3×20 mL), dried over Na$_2$SO$_4$ and concentrated in vacuo and further purified by column chromatography (ethyl acetate, silicagel) to give 1-(4-chlorophenyl)-2-(2,4-dichlorophenyl)-N-(piperidin-1-yl)-1H-imidazole-4-carboxamide (356 mg, 26% yield (based on ethyl 1-(4-chlorophenyl)-2-(2,4-dichlorophenyl)-1H-imidazole-4-carboxylate). Mass Spectrometry (MS): 449.

Analogously were prepared:
2. 1-(4-Chlorophenyl)-2-(2,4-dichlorophenyl)-N-(pyrrolidin-1-yl)-1H-imidazole-4-carboxamide; MS: 435.
3. N-(t-Butoxy)-1-(4-chlorophenyl)-2-(2,4-dichlorophenyl)-1H-imidazole-4-carboxamide; MS: 438.
4. 1-(4-Chlorophenyl)-2-(2,4-dichlorophenyl)-N-phenyl-1H-imidazole-4-carboxamide; MS: 442.
5. 1-(4-Chlorophenyl)-N-cyclohexyl-2-(2,4-dichlorophenyl)-1H-imidazole-4-carboxamide; MS: 448.
6. N-(Benzyl)-1-(4-chlorophenyl)-2-(2,4-dichlorophenyl)-N-methyl-1H-imidazole-4-carboxamide; MS: 470.
7. 1-[1-(4-Chlorophenyl)-2-(2,4-dichlorophenyl)-4-(1H-imidazolyl)carbonyl]hexahydro-1H-azepine; MS: 448.
8. 2-(4-Chlorophenyl)-1-(2,4-dichlorophenyl)-N-(piperidin-1-yl)-1H-imidazole-4-carboxamide (prepared from 2,4-dichloroaniline and 4-chlorobenzo-nitrile); MS: 449.
9. N-(t-Butoxy)-2-(4-chlorophenyl)-1-(2,4-dichlorophenyl)-1H-imidazole-4-carboxamide (prepared from 2,4-dichloroaniline and 4-chlorobenzonitrile); MS: 438.

EXAMPLE 10

Part A: Diisopropylamine (2.30 gram, 22.8 mmol) is added dropwise to anhydrous THF (100 mL) in a nitrogen atmosphere at 0° C. n-BuLi is added dropwise (7.34 mL, 2.5 M solution in hexane, 18.4 mmol). The resulting solution is cooled to −78° C. A solution of ethyl 2-(4-chlorophenyl)-1-(2,4-dichlorophenyl)-1H-imidazole-4-carboxylate (6.0 gram, 15.2 mmol) in anhydrous THF is added dropwise. The colour of the mixture changes from yellow to purple brown. The stirred mixture is warmed to −40° C. and cooled to −78° C. and allowed to stand for 30 minutes. Methyl iodide (6.44 gram, 45.4 mmol) is added dropwise and the resulting solution is stirred for 30 min at −78° C. and then allowed to attain room temperature. The resulting solution is quenched with an aqueous NH$_4$Cl solution, diethyl ether is added and the organic layer is dried over MgSO$_4$, filtered and concentrated in vacuo to give an oil (6.4 gram). This oil is purified by column chromatography (toluene/EtOAc=10/2 (v/v), silicagel) to give pure ethyl 2-(4-chlorophenyl)-1-(2,4-dichlorophenyl)-5-methyl-1H-imidazole-4-carboxylate (5.3 gram, 85% yield) as a yellow oil.

Part B: Ethyl 2-(4-chlorophenyl)-1-(2,4-dichlorophenyl)-5-methyl-1H-imidazole-4-carboxylate (0.250 gram, 0.61 mmol) and LiOH (0.052 gram, 2.17 mmol) are dissolved in H$_2$O/THF (1:1 (v/v); 50 mL) and stirred at 50° C. for one hour. The mixture is concentrated to give crude 2-(4-chlorophenyl)-1-(2,4-dichlorophenyl)-5-methyl-1H-imidazole-4-carboxylic acid. To this mixture is added SOCl$_2$ (50 mL) and the resulting mixture is heated at reflux temperature for 1 hour. The mixture is concentrated to give 2-(4-chlorophenyl)-1-(2,4-dichlorophenyl)-5-methyl-1H-imidazole-4-carbonyl chloride.

Part C: 2-(4-Chlorophenyl)-1-(2,4-dichlorophenyl)-5-methyl-1H-imidazole-4-carbonyl chloride (1.5 gram, 3.75 mmol), 1-aminopiperidine (0.725 gram, 7.25 mmol) and triethylamine (0.549 gram, 5.44 mmol) are dissolved in dichloromethane and stirred for one hour at room temperature. The mixture is washed with a saturated aqueous NaHCO$_3$ solution, dried over Na$_2$SO$_4$ and concentrated in vacuo and further purified by column chromatography (heptane/ethyl acetate=1/1 (v/v), silicagel) to give 2-(4-chlorophenyl)-1-(2,4-dichlorophenyl)-5-methyl-N-(piperidin-1-yl)-1H-imidazole-4-carboxamide (0.220 gram, 13% yield) as a white foam. MS: 463.

Analogously were prepared:
11. N-(t-Butoxy)-2-(4-chlorophenyl)-1-(2,4-dichlorophenyl)-5-methyl-1H-imidazole-4-carboxamide: MS: 452.
12. 1-(4-Chlorophenyl)-2-(2,4-dichlorophenyl)-5-methyl-N-(piperidin-1-yl)-1H-imidazole-4-carboxamide: MS: 463; Melting point: 165–167° C.
13. N-(t-Butoxy)-2-(2,4-dichlorophenyl)-1-(4-chlorophenyl)-5-methyl-1H-imidazole-4-carboxamide: MS: 452.
14. N-(t-Butoxy)-1-(4-chlorophenyl)-2-(2,4-dichlorophenyl)-5-ethyl-1H-imidazole-4-carboxamide: Amorphous. MS: 468.
15. 1-(4-Chlorophenyl)-2-(2,4-dichlorophenyl)-5-ethyl-N-(piperidin-1-yl)-1H-imidazole-4-carboxamide: MS: 477.
16. 1-(4-Bromophenyl)-N-(t-butoxy)-2-(2,4-dichlorophenyl)-5-methyl-1H-imidazole-4-carboxamide: Amorphous.
17. 1-(4-Bromophenyl)-2-(2,4-dichlorophenyl)-5-methyl-N-(piperidin-1-yl)-1H-imidazole-4-carboxamide: MP:>204° C. TLC (Silicagel, EtOAc) R$_f$=0.3.
18. 1-(4-Bromophenyl)-N-(t-butoxy)-2-(2,4-dichlorophenyl)-5-ethyl-1H-imidazole-4-carboxamide: Amorphous. TLC (Silicagel, CH$_2$Cl$_2$/acetone=9/1 (v/v)) R$_f$=0.45.
19. 1-(4-Bromophenyl)-2-(2,4-dichlorophenyl)-5-ethyl-N-(piperidin-1-yl)-1H-imidazole-4-carboxamide: MP:>140° C. TLC (Silicagel, EtOAc) R$_f$=0.4.
20. 1-(4-Bromophenyl)-N-cyclohexyl-2-(2,4-dichlorophenyl)-5-ethyl-1H-imidazole-4-carboxamide: Melting point>135–140° C.
21. 1-(4-Bromophenyl)-2-(2,4-dichlorophenyl)-5-ethyl-N-(n-pentyl)-1H-imidazole-4-carboxamide: Syrup. TLC (Silicagel, CH$_2$Cl$_2$/acetone=19/1 (v/v)) R$_f$=0.4.

EXAMPLE 22

Part A: To a stirred solution of ethyl 1-(4-bromophenyl)-2-(2,4-dichlorophenyl)-1H-imidazole-4-carboxylate (6.10 gram, 0.0139 mol) in THF (70 mL) is added LiOH (0.67 gram, 0.0278 mol) and water (70 mL). The resulting mixture is stirred for 16 hours at 50° C. to give a clear solution. After cooling to room temperature, HCl (1N solution, 28 mL) is added to give an oily precipitate which completely solidifies on continued stirring and addition of water (70 mL). The precipitate is collected by filtration, washed with water and dried in vacuo to give 1-(4-bromophenyl)-2-(2,4-dichlorophenyl)-1H-imidazole-4-carboxylic acid (4.92 gram, 86% yield). Melting point: 138–142° C.

Part B: To a stirred suspension of 1-(4-bromophenyl)-2-(2,4-dichlorophenyl)-1H-imidazole-4-carboxylic acid (1.23 gram, 2.99 mmol) in dry acetonitrile (40 mL) is successively added diisopropylethylamine (DIPEA) (1.15 mL, 6.6 mmol), O-benzotriazol-1-yl-N,N,N',N'-tetramethyluronium hexafluorophos-phate (HBTU) (1.36 gram, 3.6 mmol) and 1-aminopiperidine (0.39 mL, 3.6 mmol). After stirring for 16 hours, the resulting mixture is concentrated in vacuo. The residue is dissolved in ethylacetate and an aqueous NaHCO$_3$ solution is added. The ethylacetate layer is collected, washed with water and brine, dried over Na$_2$SO$_4$, filtered and concentrated in vacuo to give a crude solid. This solid is further purified by recrystallisation from acetonitrile to give 1-(4-bromophenyl)-2-(2,4-dichlorophenyl)-N-(piperidin-1-yl)-1H-imidazole-4-carboxamide (830 mg, 56% yield). Melting point: 219–221° C.

Analogously were prepared:

23. N-(t-Butoxy)-1-(4-bromophenyl)-2-(2,4-dichlorophenyl)-1H-imidazole-4-carboxamide. Amorphous. TLC (Silicagel, Et$_2$O) R$_f$=0.3.
24. 1-(4-Bromophenyl)-2-(2,4-dichlorophenyl)-N-(pyrrolidin-1-yl)-1H-imidazole-4-carboxamide. Melting point: 238–240° C.
25. N-(Azepan-1-yl)-1-(4-bromophenyl)-2-(2,4-dichlorophenyl)-1H-imidazole-4-carboxamide. Melting point: 201–204° C.
26. 1-(4-Chlorophenyl)-2-(2,4-dichlorophenyl)-N-(hexahydrocyclopenta[c]pyrrol-2(1H)-yl)-1H-imidazole-4-carboxamide. MS: 475.
27. 1-(4-Chlorophenyl)-2-(2,4-dichlorophenyl)-N-(4-fluorobenzyl)-1H-imidazole-4-carboxamide. MS: 474.
28. 1-(4-Chlorophenyl)-2-(2-methoxy-4-chlorophenyl)-N-(piperidin-1-yl)-1H-imidazole-4-carboxamide. Melting point: 220° C.
29. 1-(4-Chlorophenyl)-N-cyclohexyl-2-(2-methoxy-4-chlorophenyl)-1H-imidazole-4-carboxamide. Melting point: 177–179° C.
30. 1-(4-Chlorophenyl)-2-(2-fluoro-4-chlorophenyl)-N-(piperidin-1-yl)-1H-imidazole-4-carboxamide. Melting point: 217–218° C.
31. 2-(2,4-Dichlorophenyl)-1-(4-fluorophenyl)-N-(piperidin-1-yl)-1H-imidazole-4-carboxamide. Melting point: 175–176° C.
32. N-Cyclohexyl-2-(2,4-dichlorophenyl)-1-(4-fluorophenyl)-1H-imidazole-4-carboxamide. Melting point: 184–185° C.
33. N-Cyclohexyl-2-(2-fluoro-4-chlorophenyl)-1-(4-chlorophenyl)-1H-imidazole-4-carboxamide. Melting point: 157–159° C.
34. 1-(4-Chlorophenyl)-2-(2-methoxy-4-chlorophenyl)-N-(n-pentyl)-1H-imidazole-4-carboxamide. Melting point: 115° C.
35. 2-(2,4-Dichlorophenyl)-1-(4-methoxyphenyl)-N-(piperidin-1-yl)-1H-imidazole-4-carboxamide. Melting point: 178–179° C.
36. N-Cyclohexyl-2-(2,4-dichlorophenyl)-1-(4-methoxyphenyl)-1H-imidazole-4-carboxamide. Melting point: 175–176° C.
37. 1-(4-Chlorophenyl)-2-(2,4-dichlorophenyl)-N,N-diethyl-1H-imidazole-4-carboxamide. Melting point: 177–179° C.
38. 1-(4-Chlorophenyl)-N-cyclohexyl-2-(2-trifluoromethyl-4-chlorophenyl)-1H-imidazole-4-carboxamide. Melting point: 172° C.
39. 1-(4-Chlorophenyl)-N-(piperidin-1-yl)-2-(2-trifluoromethyl-4-chlorophenyl)-1H-imidazole-4-carboxamide. Melting point: 219° C.
40. N-(1-Adamantyl)-1-(4-chlorophenyl)-2-(2-trifluoromethyl-4-chlorophenyl)-1H-imidazole-4-carboxamide. Melting point: 288° C.
41. 1-(4-Chlorophenyl)-N-(2,2,2-trifluoroethyl)-2-(2-trifluoromethyl-4-chlorophenyl)-1H-imidazole-4-carboxamide. Melting point: 149° C.
42. 2-(2,4-Dichlorophenyl)-1-(pyridin-3-yl)-N-(piperidin-1-yl)-1H-imidazole-4-carboxamide. Melting point: 165–170° C.
43. N-Cyclohexyl-2-(2,4-dichlorophenyl)-1-(pyridin-3-yl)-1H-imidazole-4-carboxamide. Melting point: 195° C.
44. 2-(2,4-Dichlorophenyl)-1-(pyridin-3-yl)-N-(n-pentyl)-1H-imidazole-4-carboxamide. Melting point: 117° C.

EXAMPLE 45

Part A: 2,4-Dichlorobenzoyl chloride (40.0 g, 0.19 mol) is dissolved in tetrahydrofuran (1 L). To the resulting stirred solution is successively added diisopropylethylamine (DIPEA) (73.4 mL, 2.2 molar equivalent) and 4-(trifluoromethyl)phenylamine (30.7 g, 0.19 mol). After one hour the mixture is concentrated in vacuo to give an oil. This oil is crystallised from ethanol to give pure 2,4-dichloro-N-(4-(trifluoromethyl)phenyl)benzamide (53.2 g, 83% yield). $^1$H-NMR (200 MHz, DMSO-d$_6$): δ 10.90 (br s, 1H), 7.91 (br d, J=8 Hz, 2H), 7.63–7.77 (m, 4H), 7.57 (dt, J=8 Hz, J=2 Hz, 1H).

Part B: 2,4-Dichloro-N-(4-(trifluoromethyl)phenyl)benzamide (19.0 g, 0.057 mol) is dissolved in benzene (150 mL) and PCl$_5$ (13.0 g, 1.1 molar equivalent) is added. The resulting mixture is heated at reflux temperature for two hours, allowed to attain room temperature and concentrated in vacuo to give a residue. The residue is dissolved in anhydrous THF, cooled to 0° C. and transferred into an autoclave. Excess NH$_3$ is quickly added from a lecture bottle and the mixture is stirred at room temperature for 50 hours. A mixture of ethylacetate and aqueous NaHCO$_3$ is added. The ethylacetate layer is collected, dried over Na$_2$SO$_4$, filtered and concentrated in vacuo. The resulting oil is purified by column chromatography (diethyl ether/petroleum ether=1/1 (v/v), silicagel) to give pure 2,4-dichloro-N-(4-(trifluoromethyl)phenyl)benzene-carboxamidine (16.9 g, 89% yield). Melting point: 108–109° C.

Part C: 2,4-Dichloro-N-(4-(trifluoromethyl)phenyl)benzenecarboxamidine (15.0 g, 0.0450 mol) is dissolved in 2-propanol and ethyl 3-bromo-2-oxobutanoate (20.8 g, 2 molar equivalent) and NaHCO$_3$ are successively added. The resulting mixture is heated at reflux temperature for 40 hours and allowed to attain room temperature. The 2-propanol is removed in vacuo, ethyl acetate is added to the residue and the resulting organic layer is washed with NaHCO$_3$ (5% aqueous solution). The ethylacetate layer is collected, dried over Na$_2$SO$_4$, filtered and concentrated in vacuo. The resulting oil is purified by column chromatography (diethyl ether/petroleum ether=1/3 (v/v), silicagel) and further purified by crystallisation from cyclohexane to give ethyl 2-(2,4-dichlorophenyl)-5-methyl-1-(4-(trifluoromethyl)phenyl)-1H-imidazole-4-carboxylate (10.45 g, 52% yield) as a yellow solid. Melting point: 160–162° C.

Part D: The formed ethyl 2-(2,4-dichlorophenyl)-5-methyl-1-(4-(trifluoromethyl)phenyl)-1H-imidazole-4-carboxylate is converted to 2-(2,4-dichlorophenyl)-5-methyl-1-(4-(trifluoromethyl)phenyl)-1H-imidazole-4-carboxylic acid (melting point: 224–226° C.), which carboxylic acid is converted to 2-(2,4-dichlorophenyl)-5-methyl-N-(piperidin-1-yl)-1-(4-(trifluoromethyl)phenyl)-1H-imidazole-4-carboxamide (melting point: 173–174° C.) according to the procedure described in example 22 above.

Analogously were prepared 46. 2-(2,4-dichlorophenyl)-N-(piperidin-1-yl)-1-(4-(trifluoromethyl)phenyl)-1H-imidazole-4-carboxamide. Melting point:>200° C. (decomposition).
47. N-Cyclohexyl-2-(2,4-dichlorophenyl)-5-methyl-1-(4-(trifluoromethyl)phenyl)-1H-imidazole-4-carboxamide. Melting point: 178–179° C.
48. N-Cyclohexyl-2-(2,4-dichlorophenyl)-1-(4-(trifluoromethyl)phenyl)-1H-imidazole-4-carboxamide. Melting point: 199–200° C.

EXAMPLE 49

Part A: N-(4-methoxyphenyl)-2,4-dichlorobenzenecarboxamidine (15.0 gram, 50.8 mmol) is dissolved in 2-propanol and ethyl 3-bromo-2-oxobutanoate (23.5 g, 2 molar equivalents) and NaHCO$_3$ (8.5 gram, 2 molar equivalents) are successively added. The resulting mixture is heated at reflux temperature for 40 hours and allowed to attain room temperature. The 2-propanol is removed in vacuo, ethyl acetate is added to the residue and the resulting organic layer is washed with NaHCO$_3$ (5% aqueous solution). The ethylacetate layer is collected, dried over Na$_2$SO$_4$, filtered and concentrated in vacuo. The resulting oil is purified by column chromatography (diethyl ether/petroleum ether=1/3 (v/v), silicagel) to give ethyl 2-(2,4-dichlorophenyl)-5-methyl-1-(4-methoxy-phenyl)-1H-imidazole-4-carboxylate (8.61 g, 42% yield) as a solid. $^1$H-NMR (200 MHz, CDCl$_3$): δ 7.33 (d, J=8 Hz, 1H), 7.27 (d, J=2 Hz, 1H), 7.18 (dd, J=8 Hz, J=2 Hz, 1H), 7.03 (dt, J=8 Hz, J=2 Hz, 2H), 6.85 (dt, J=8 Hz, J=2 Hz, 2H), 4.42 (q, J=7 Hz, 2H), 3.80 (s, 3H), 2.43 (s, 3H), 1.43 (t, J=7 Hz, 3H).

Part B: To a stirred solution of ethyl 2-(2,4-dichlorophenyl)-5-methyl-1-(4-methoxyphenyl)-1H-imidazole-4-carboxylate (8.00 gram, 0.0198 mol) in THF (80 mL) is added LiOH (0.59 gram, 2 molar equivalents) and water (80 mL). The resulting mixture is stirred for 16 hours at 80° C. After cooling to room temperature, HCl (2N solution, 12.3 mL) is added to give an oily precipitate. After addition of water and extraction with ethylacetate, the ethylacetate layer is collected, dried over Na$_2$SO$_4$, filtered and concentrated in vacuo. The residue is crystallised from diisopropyl ether and dried to give 2-(2,4-dichlorophenyl)-5-methyl-1-(4-methoxyphenyl)-1H-imidazole-4-carboxylic acid (4.04 gram, 87% yield) as a pale grey solid. Melting point: 189–191° C.

Part C: To 2-(2,4-dichlorophenyl)-5-methyl-1-(4-methoxyphenyl)-1H-imidazole-4-carboxylic acid (1.00 gram, 2.65 mmol) in dry acetonitrile (25 mL) is successively added diisopropylethylamine (DIPEA) (1.02 mL, 2.2 molar equivalents), O-benzotriazol-1-yl-N,N,N',N'-tetramethyluronium hexafluoro-phosphate (HBTU) (1.21 gram, 1.2 molar equivalents) and the resulting solution is stirred for 15 minutes. Cyclohexylamine (0.36 mL, 1.2 molar equivalents) is added. After stirring for 50 hours, the resulting mixture is concentrated in vacuo. The residue is dissolved in dichloromethane and an aqueous NaHCO$_3$ solution is added. The dichloromethane layer is collected, dried over Na$_2$SO$_4$, filtered and concentrated in vacuo. The residue is further purified by column chromatography (gradient: dichloromethane=>dichloromethane/methanol=99/1 (v/v), silicagel) to give N-(1-cyclohexyl)-2-(2,4-dichlorophenyl)-5-methyl-1-(4-methoxyphenyl)-1H-imidazole-4-carboxamide (1.03 gram, 85% yield). Melting point: 160–161° C.

Analogously were prepared:

50. 1-(4-Chlorophenyl)-2-(2,4-dichlorophenyl)-N,N,5-trimethyl-1H-imidazole-4-carboxamide. Melting point: 101–104° C.
51. 1-(5-Chloropyridin-2-yl)-2-(2,4-dichlorophenyl)-5-methyl-N-(piperidin-1-yl)-1H-imidazole-4-carboxamide. MS: 464 (MH$^+$).
52. 1-(5-Chloropyridin-2-yl)-2-(2,4-dichlorophenyl)-5-methyl-N-(4-morpholinyl)-1H-imidazole-4-carboxamide. MS: 466 (MH$^+$).
53. N-(1-Azepanyl)-1-(5-Chloropyridin-2-yl)-2-(2,4-dichlorophenyl)-5-methyl-1H-imidazole-4-carboxamide. MS: 478 (MH$^+$).
54. 1-(5-Chloropyridin-2-yl)-N-cyclohexyl-2-(2,4-dichlorophenyl)-5-methyl-1H-imidazole-4-carboxamide. MS: 463.
55. 1-(5-Chloropyridin-2-yl)-2-(2,4-dichlorophenyl)-5-methyl-N-(n-pentyl)-1H-imidazole-4-carboxamide. MS: 451.
56. 1-(5-Chloropyridin-2-yl)-2-(2,4-dichlorophenyl)-N-(4-fluorobenzyl)-5-methyl-1H-imidazole-4-carboxamide. MS: 489. Melting point: 123–126° C.
57. 1-(4-Chlorophenyl)-N-cyclohexyl-5-methyl-2-(2-trifluoromethyl-4-chlorophenyl)-1H-imidazole-4-carboxamide. Melting point: 212° C.
58. 1-(4-Chlorophenyl)-5-methyl-N-(piperidin-1-yl)-2-(2-trifluoromethyl-4-chlorophenyl)-1H-imidazole-4-carboxamide. Melting point: 165° C.
59. 1-(4-Chlorophenyl)-2-(2-methoxy-4-chlorophenyl)-5-methyl-N-(n-pentyl)-1H-imidazole-4-carboxamide. Melting point: 131° C.
60. 1-(4-Chlorophenyl)-2-(2-methoxy-4-chlorophenyl)-5-methyl-N-(piperidin-1-yl)-1H-imidazole-4-carboxamide. Melting point:>256° C.
61. N-Cyclohexyl-1-(4-chlorophenyl)-2-(2-methoxy-4-chlorophenyl)-5-methyl-1H-imidazole-4-carboxamide. Melting point: 201° C.
62. 2-(2,4-Dichlorophenyl)-1-(4-fluorophenyl)-5-methyl-N-(piperidin-1-yl)-1H-imidazole-4-carboxamide. Melting point: 223–224° C.
63. 2-(2,4-Dichlorophenyl)-5-methyl-1-(4-methoxyphenyl)-N-(piperidin-1-yl)-1H-imidazole-4-carboxamide. Melting point:>90° C. (decomposition).
64. N-Cyclohexyl-1-(4-fluorophenyl)-2-(2,4-dichlorophenyl)-5-methyl-1H-imidazole-4-carboxamide. Melting point: 229–230° C.
65. 1-(4-Chlorophenyl)-5-methyl-N-(n-pentyl)-2-(2-trifluoromethyl-4-chlorophenyl)-1H-imidazole-4-carboxamide. Amorphous.
66. 1-(4-Chlorophenyl)-2-(2-fluoro-4-chlorophenyl)-5-methyl-N-(piperidin-1-yl)-1H-imidazole-4-carboxamide. Melting point: 195° C.
67. 1-(4-Chlorophenyl)-2-(2-fluoro-4-chlorophenyl)-5-methyl-N-(n-pentyl)-1H-imidazole-4-carboxamide. Melting point: 115° C.
68. 1-(4-Chlorophenyl)-N-(cyclohexyl)-2-(2-fluoro-4-chlorophenyl)-5-methyl-1H-imidazole-4-carboxamide. Melting point: 188° C.
69. 1-(4-Chlorophenyl)-N-(cyclohexyl)-2-(1,5-dimethyl-1H-pyrrol-2-yl)-5-methyl-1H-imidazole-4-carboxamide. Melting point: 188–189° C.
70. 1-(4-Chlorophenyl)-2-(1,5-dimethyl-1H-pyrrol-2-yl)-5-methyl-N-(piperidin-1-yl)-1H-imidazole-4-carboxamide. Melting point: 208–210° C.
71. 2-(2-Chlorophenyl)-1-(3-fluorophenyl)-5-methyl-N-(piperidin-1-yl)-1H-imidazole-4-carboxamide. Melting point: 236–238° C.
72. 2-(2-Chlorophenyl)-1-(3-fluorophenyl)-5-methyl-N-(n-pentyl)-1H-imidazole-4-carboxamide. Melting point: 97–102° C.
73. 2-(2-Chlorophenyl)-N-cyclohexyl-1-(3-fluorophenyl)-5-methyl-1H-imidazole-4-carboxamide. Melting point: 180–182.5° C.
74. 2-(2-Chlorophenyl)-1-(3-fluorophenyl)-N-(2-(4-fluorophenyl)ethyl)-5-methyl-1H-imidazole-4-carboxamide. Melting point: 123.5–126° C.

75. 1-(5-Chloropyridin-2-yl)-2-(2,4-dichlorophenyl)-5-ethyl-N-(piperidin-1-yl)-1H-imidazole-4-carboxamide. Melting point: 146° C.
76. 1-(5-Chloropyridin-2-yl)-2-(2,4-dichlorophenyl)-5-ethyl-N-(4-morpholinyl)-1H-imidazole-4-carboxamide. Melting point: 223° C.
77. N-(1-Azepanyl)-1-(5-Chloropyridin-2-yl)-2-(2,4-dichlorophenyl)-5-ethyl-1H-imidazole-4-carboxamide. Melting point: 177° C.
78. 1-(5-Chloropyridin-2-yl)-N-cyclohexyl-2-(2,4-dichlorophenyl)-5-ethyl-1H-imidazole-4-carboxamide. Melting point: 149° C.
79. 1-(5-Chloropyridin-2-yl)-2-(2,4-dichlorophenyl)-5-ethyl-N-(n-pentyl)-1H-imidazole-4-carboxamide. Melting point: Oil.
80. 1-(5-Chloropyridin-2-yl)-2-(2,4-dichlorophenyl)-5-ethyl-N-(4-fluorophenylmethyl)-1H-imidazole-4-carboxamide. MP: amorphous.
81. 1-(4-Chlorophenyl)-2-(2,4-dichlorophenyl)-N-(hexahydrocyclopenta-[c]pyrrol-2(1H)-yl)-5-methyl-1H-imidazole-4-carboxamide. MP: 143–146° C.
82. 1-(4-Chlorophenyl)-2-(2,4-dichlorophenyl)-5-methyl-N-phenyl-1H-imidazole-4-carboxamide. Melting point: 91–95° C.
83. 1-(4-Chlorophenyl)-2-(2,4-dichlorophenyl)-5-methyl-N-(tetrahydro-2H-pyran-2-yloxy)-1H-imidazole-4-carboxamide. Melting point: 128–133° C.
84. N-(Exo-bicyclo[2.2.1]hept-2-yl)-1-(4-chlorophenyl)-2-(2,4-dichlorophenyl)-5-methyl-1H-imidazole-4-carboxamide. Melting point: 194–195° C.
85. 1-(4-Chlorophenyl)-2-(2,4-dichlorophenyl)-N-(2-fluoroethyl)-5-methyl-1H-imidazole-4-carboxamide. Melting point: 128–133° C.
86. 1-(4-Chlorophenyl)-2-(2,4-dichlorophenyl)-N-(trans-4-hydroxycyclohexyl)-5-methyl-1H-imidazole-4-carboxamide. Melting point: 160° C. (dec.).
87. 1-{[1-(4-Chlorophenyl)-2-(2,4-dichlorophenyl)-5-methyl-1H-imidazol-4-yl]carbonyl}-4-hydroxypiperidine. Melting point: Amorphous.
88. 1-{[1-(4-Chlorophenyl)-2-(2,4-dichlorophenyl)-5-methyl-1H-imidazol-4-yl]carbonyl}-1,2,3,4-tetrahydroisoquinoline. Melting point: 143–146° C.
89. N-(Endo-bicyclo[2.2.1]hept-2-yl)-1-(4-chlorophenyl)-2-(2,4-dichlorophenyl)-5-methyl-1H-imidazole-4-carboxamide. Melting point: 194–195° C.
90. 1-(4-Chlorophenyl)-2-(2,4-dichlorophenyl)-N-(4-fluorobenzyl)-5-methyl-1H-imidazole-4-carboxamide. Melting point: 165–166° C.
91. 1-(4-Chlorophenyl)-2-(2,4-dichlorophenyl)-5-methyl-N-(n-pentyl)-1H-imidazole-4-carboxamide. Oil.
92. N-(Azepan-1-yl)-1-(4-chlorophenyl)-2-(2,4-dichlorophenyl)-5-methyl-1H-imidazole-4-carboxamide. Melting point: 147–149° C.
93. 1-(4-Chlorophenyl)-2-(2,4-dichlorophenyl)-5-methyl-N-(pyrrolidin-1-yl)-1H-imidazole-4-carboxamide. Melting point: 205–206° C.
94. 1-(4-Chlorophenyl)-2-(2,4-dichlorophenyl)-5-methyl-N-(morpholin-4-yl)-1H-imidazole-4-carboxamide. Melting point: 225° C. (dec.).
95. 2-(2,5-Dichlorophenyl)-5-methyl-1-phenyl-N-(piperidin-1-yl)-1H-imidazole-4-carboxamide. Melting point: 227° C.
96. N-Cyclohexyl-2-(2,5-dichlorophenyl)-5-methyl-1-phenyl-1H-imidazole-4-carboxamide. Melting point: 236° C.
97. N-Cyclohexyl-2-(2,4-dichlorophenyl)-1-(2,5-difluorophenyl)-5-ethyl-1H-imidazole-4-carboxamide. Melting point: 144–146° C.
98. N-Cyclohexyl-2-(2,4-dichlorophenyl)-1-(2,5-difluorophenyl)-5-methyl-1H-imidazole-4-carboxamide. Melting point: 206–208° C.
99. N-Cyclohexyl-2-(1,5-dimethyl-1H-pyrrol-2-yl)-5-ethyl-1-phenyl-1H-imidazole-4-carboxamide. Melting point: 195–196° C.
100. N-Cyclohexyl-2-(2,5-dichlorophenyl)-5-ethyl-1-phenyl-1H-imidazole-4-carboxamide. Melting point: 198–199° C.
101. 2-(2,5-Dichlorophenyl)-5-ethyl-1-phenyl-N-(piperidin-1-yl)-1H-imidazole-4-carboxamide. Melting point: 207–208° C.
102. 1-(4-Chlorophenyl)-5-methyl-2-(3-methylpyridin-2-yl)-N-(piperidin-1-yl)-1H-imidazole-4-carboxamide. Melting point: 211–213° C.
103. 1-(4-Chlorophenyl)-N-cyclohexyl-5-methyl-2-(3-methylpyridin-2-yl)-1H-imidazole-4-carboxamide. Melting point: 188–190° C.
104. 1-(4-Chlorophenyl)-2-(2,4-dichlorophenyl)-5-methyl-N-(3-(trifluoromethyl)phenyl)-1H-imidazole-4-carboxamide. Melting point: 177° C.
105. 1-(4-Chlorophenyl)-2-(2,4-dichlorophenyl)-5-methyl-N-(3-(trifluoromethyl)benzyl)-1H-imidazole-4-carboxamide. Melting point: 138–140° C.
106. 1-(4-Chlorophenyl)-2-(2,4-dichlorophenyl)-5-methyl-N-(4-(trifluoromethyl)benzyl)-1H-imidazole-4-carboxamide. Melting point: 232° C.
107. 1-(4-Chlorophenyl)-N-cyclopentyl-2-(2,4-dichlorophenyl)-5-methyl-1H-imidazole-4-carboxamide. Melting point: 172° C.
108. 1-(4-Chlorophenyl)-N-cycloheptyl-2-(2,4-dichlorophenyl)-5-methyl-1H-imidazole-4-carboxamide. Melting point: 154–156° C.

EXAMPLE 109

Part A: Ethyl 1-(4-bromophenyl)-2-(2,4-dichlorophenyl)-1H-imidazole-4-carboxylate is converted to ethyl 1-(4-bromophenyl)-5-chloro-2-(2,4-dichlorophenyl)-1H-imidazole-4-carboxylate analogously to a published procedure (N. Kudo et al., *Chem. Pharm. Bull.* 1999, 47, 857–868) using excess of $SO_2Cl_2$ in dichloroethane at reflux temperature for 50 hours.

Part B: Ethyl 1-(4-bromophenyl)-5-chloro-2-(2,4-dichlorophenyl)-1H-imidazole-4-carboxylate is converted to 1-(4-bromophenyl)-5-chloro-2-(2,4-dichloro-phenyl)-N-(piperidin-1-yl)-1H-imidazole-4-carboxamide (melting point: >150° C.; $R_f$ (Silicagel, EtOAc)~0.35) analogously to the procedure described in example 22 above. $^1$H-NMR (400 MHz, $CDCl_3$): δ 7.85 (br s, 1H), 7.52 (dt, J=8 Hz, J=2 Hz, 2H), 7.26–7.36 (m, 3H), 7.01 (dt, J=8 Hz, J=2 Hz, 2H), 2.85–2.92 (m, 4H), 1.72–1.80 (m, 4H), 1.40–1.44 (m, 2H).

EXAMPLE 110

Part A: To a stirred solution of 1-(4-chlorophenyl)-2-(2,4-dichlorophenyl)-1H-imidazole-4-carboxylic acid (18.38 gram, 50 mmol) in toluene (200 mL) in a nitrogen atmosphere is added N,N-dimethylformamide di-tert-butyl acetal (50 mL) and the resulting mixture is heated at 80° C. for 4 hours. After cooling to room temperature the reaction mixture is concentrated and diethyl ether is added. The resulting solution is twice washed with water, dried over MgSO$_4$, filtered and concentrated in vacuo. The residue is crystallised from diisopropyl ether to give pure tert-butyl 1-(4-chlorophenyl)-2-(2,4-dichlorophenyl)-1H-imidazole-4-carboxylate (10.35 gram, 49% yield). Melting point: 179–181° C.

Part B:

Lithium diisopropyl amide (LDA) (5.25 mL of a 2 M solution in THF, 0.0105 mol) is added dropwise to a cooled solution (−70° C.) of tert-butyl 1-(4-chlorophenyl)-2-(2,4-dichlorophenyl)-1H-imidazole-4-carboxylate (4.24 gram, 0.010 mol) in anhydrous THF (80 mL) in a nitrogen atmosphere and the resulting mixture is stirred for one hour. A solution of p-toluenesulfonyl cyanide (1.88 gram, 0.011 mol) in anhydrous THF (20 mL) is added dropwise and the resulting red solution is stirred for one hour at −70° C. and then allowed to attain room temperature. Diethyl ether is added and the resulting solution is quenched with water and filtered over hyflo. The organic layer is collected and washed with water, dried over MgSO$_4$, filtered and concentrated in vacuo to give an oil. This oil is purified by column chromatography (dichloromethane, silicagel) to give 3.4 gram of tert-butyl 1-(4-chlorophenyl)-5-cyano-2-(2,4-dichlorophenyl)-1H-imidazole-4-carboxylate. Recrystallisation from diisopropyl ether gave crystalline tert-butyl 1-(4-chlorophenyl)-5-cyano-2-(2,4-dichlorophenyl)-1H-imidazole-4-carboxylate (2.57 gram, 57% yield). Melting point: 210–212° C.

Analogously was prepared:

Tert-butyl 1-(4-chlorophenyl)-2-(2,4-dichlorophenyl)-5-methyl-1H-imidazole-4-carboxylate. $^1$H-NMR (400 MHz, CDCl$_3$): δ 7.38 (d, J=8 Hz, 1H), 7.34 (dt, J=8 Hz, J=2 Hz, 2H), 7.27 (d, J=2 Hz, 1H), 7.22 (dd, J=8 Hz, J=2 Hz, 1H), 7.03 (dt, J=8 Hz, J=2 Hz, 2H), 2.40 (s, 3H), 1.63 (s, 9H).

Part C:

To a solution of tert-butyl 1-(4-chlorophenyl)-2-(2,4-dichlorophenyl)-5-cyano-1H-imidazole-4-carboxylate (2.57 gram, 5.73 mmol) in dichloromethane (40 mL) is added trifluoroacetic acid and the resulting solution is stirred at room temperature for 20 hours and concentrated in vacuo. The residue is crystallised from diisopropyl ether to give pure 1-(4-chlorophenyl)-5-cyano-2-(2,4-dichlorophenyl)-1H-imidazole-4-carboxylic acid (1.95 gram, 87% yield). Melting point: 200–202° C. (dec.).

Part D:

1-(4-Chlorophenyl)-5-cyano-2-(2,4-dichlorophenyl)-1H-imidazole-4-carboxylic acid is converted to 1-(4-chlorophenyl)-5-cyano-2-(2,4-dichlorophenyl)-N-(piperidin-1-yl)-1H-imidazole-4-carboxamide in 60% yield, analogously to the procedure described in example 22, part B herein above. Melting point: 231–233.5° C.

Analogously were prepared:

111. 1-(4-Chlorophenyl)-2-(2,4-dichlorophenyl)-5-iodo-N-(piperidin-1-yl)-1H-imidazole-4-carboxamide. Melting point: 196–201° C.
112. 1-(4-Chlorophenyl)-N-cyclohexyl-2-(2,4-dichlorophenyl)-5-iodo-1H-imidazole-4-carboxamide. Melting point: 226–230° C.
113. 1-(4-Chlorophenyl)-5-cyano-N-cyclohexyl-2-(2,4-dichlorophenyl)-1H-imidazole-4-carboxamide. Melting point: 157–158° C.

EXAMPLE 114

Synthesis of 1-(4-chlorophenyl)-2-(2,4-dichlorophenyl)-5-fluoromethyl-N-(piperidin-1-yl)-1H-imidazole-4-carboxamide

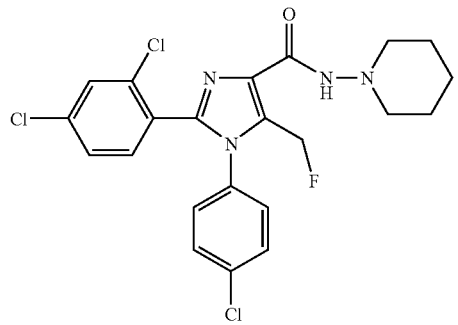

Part A: Ethyl 5-Bromomethyl-1-(4-chlorophenyl)-2-(2,4-dichlorophenyl)-1H-imidazole-4-carboxylate. To a magnetically stirred mixture of ethyl 1-(4-chlorophenyl)-2-(2,4-dichlorophenyl)-5-methyl-1H-imidazole-4-carboxylate (2.05 g, 5.00 mmol) in CCl$_4$ (25 mL) was added N-bromosuccinimide (NBS) (1.34 g, 7.53 mmol) and dibenzoyl peroxide (10.0 mg, assay 75%, 0.0310 mmol) and the resulting mixture was refluxed for 38 hours. The formed precipitate was removed by filtration. The filtrate was successively washed with brine and water, dried over MgSO$_4$, filtered and concentrated in vacuo. The residue was purified by flash chromatography (CH$_2$Cl$_2$/acetone=98/2 (v/v)) to give ethyl 5-bromomethyl-1-(4-chlorophenyl)-2-(2,4-dichlorophenyl)-1H-imidazole-4-carboxylate (1.29 g, 53% yield) as an amorphous solid, $^1$H-NMR (200 MHz, CDCl$_3$): δ 1.45 (t, J=7 Hz, 3H), 4.48 (q, J=7 Hz, 2H), 4.72 (s, 2H), 7.18–7.43 (m, 7H).

Part B: Ethyl 1-(4-chlorophenyl)-2-(2,4-dichlorophenyl)-5-fluoromethyl-1H-imidazole-4-carboxylate. To a magnetically stirred mixture of ethyl 5-bromomethyl-1-(4-chlorophenyl)-2-(2,4-dichlorophenyl)-1H-imidazole-4-carboxylate (5.46 g, 11.18 mmol) in anhydrous CH$_3$CN (150 mL) was added anhydrous potassium fluoride (KF) (6.4 g, 13.1 mmol) and 4,7,13,16,21,24-hexaoxa-1,10-diazabicyclo[8.8.8]hexacosane (Kryptofix) (4.0 g, 10.6 mmol). The resulting mixture was refluxed for 1 hour and concentrated in vacuo. EtOAc was added to the residue and the resulting solution was washed with water, dried over MgSO$_4$, filtered and concentrated. The residue was purified by flash chromatography (CH$_2$Cl$_2$/acetone=99/1 (v/v)) and recrystallized from diisopropyl ether to give ethyl 1-(4-chlorophenyl)-2-(2,4-dichlorophenyl)-5-fluoromethyl-1H-imidazole-4-carboxylate (1.88 g, 39% yield), mp 124–125° C.; $^1$H-NMR (200 MHz, CDCl$_3$): δ 1.45 (t, J=7 Hz, 3H), 4.47 (q, J=7 Hz, 2H), 5.59 (d, J=48 Hz, 2H), 7.15 (br d, J=8 Hz, 2H), 7.20–7.42 (m, 5H).

Part C: 1-(4-Chlorophenyl)-2-(2,4-dichlorophenyl)-5-fluoromethyl-1H-imidazole-4-carboxylic acid. To a magnetically stirred mixture of ethyl 1-(4-chlorophenyl)-2-(2,4-dichlorophenyl)-5-fluoromethyl-1H-imidazole-4-carboxylate (1.88 g, 4.40 mmol) in MeOH (50 mL) was added NaOH (10 mL of a 4 N solution, 40.0 mmol). The resulting mixture was stirred at room temperature for 10 minutes and and poured onto HCl (150 mL of a 1 N solution, 0.150 mol). The formed precipitate was collected by filtration, washed with H₂O and dried at 60° C. in vacuo to yield 1-(4-chlorophenyl)-2-(2,4-dichlorophenyl)-5-fluoromethyl-1H-imidazole-4-carboxylic acid (1.74 g, 99% yield), mp 187–190° C. (dec); ¹H-NMR (200 MHz, CDCl₃): δ 3.10 (br s, 1H), 5.60 (d, J=48 Hz, 2H), 7.15 (br d, J~8 Hz, 2H), 7.20–7.45 (m, 5H).

Part D: 1-(4-Chlorophenyl)-2-(2,4-dichlorophenyl)-5-fluoromethyl-N-(piperidin-1-yl)-1H-imidazole-4-carboxamide. 1-(4-Chlorophenyl)-2-(2,4-dichlorophenyl)-5-fluoromethyl-N-(piperidin-1-yl)-1H-imidazole-4-carboxamide was obtained by reacting 1-(4-chlorophenyl)-2-(2,4-dichlorophenyl)-5-fluoromethyl-1H-imidazole-4-carboxylic acid (0.87 g, 2.18 mmol), diisopropylethylamine (DIPEA) (0.84 mL, 4.80 mmol), O-benzotriazol-1-yl-N,N,N',N'-tetramethyluronium hexafluorophosphate (HBTU) (0.99 g, 2.62 mmol) and 1-aminopiperidine (0.28 mL, 2.62 mmol) for 16 hours at room temperature. The resulting mixture was concentrated in vacuo. The residue was dissolved in ethyl acetate, successively washed with aqueous NaHCO₃ solution, water and brine, dried over Na₂SO₄, filtered and concentrated to give a crude solid. This solid was further purified by flash chromatography. 1-(4-Chlorophenyl)-2-(2,4-dichlorophenyl)-5-fluoromethyl-N-(piperidin-1-yl)-1H-imidazole-4-carboxamide was obtained in 64% yield, mp 162–163° C.; ¹H-NMR (600 MHz, DMSO-d₆) δ 1.35–1.41 (m, 2H), 1.61–1.66 (m, 4H), 2.80–2.84 (m, 4H), 5.63 (d, J=48 Hz, 2H), 7.36 (d, J=8 Hz, 2H), 7.44 (dd, J=8 and 2 Hz, 1H), 7.48 (d, J=8 Hz, 2H), 7.55 (d, J=2 Hz, 1H), 7.67 (d, J=8 Hz, 1H), 9.10 (s, 1H); HRMS (C₂₂H₂₁Cl₃FN₄O) [M+H]⁺: found m/z 481.0760, calcd 481.0765.

EXAMPLE 115

Synthesis of 1-(4-chlorophenyl)-2-(2,4-dichlorophenyl)-5-hydroxymethyl-N-(piperidin-1-yl)-1H-imidazole-4-carboxamide

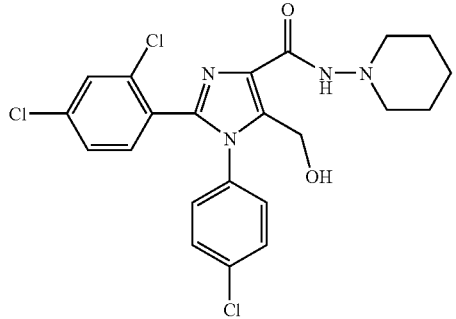

Part A: 1-(4-Chlorophenyl)-2-(2,4-dichlorophenyl)-5-hydroxymethyl-1H-imidazole-4-carboxylic acid. To a magnetically stirred mixture of ethyl 5-bromomethyl-1-(4-chlorophenyl)-2-(2,4-dichlorophenyl)-1H-imidazole-4-carboxylate (3.03 g, 6.20 mmol) in THF (45 mL) was added NaOH (45 mL of a 2 N solution, 90.0 mmol). The resulting mixture was refluxed for 16 hours. The mixture was carefully poured onto cold HCl (100 mL of a 1 N solution, 0.100 mol) and extracted with EtOAc. The EtOAc layer was separated, washed with water, dried over MgSO₄, filtered and concentrated to give a syrup (2.54 g). The syrup was crystallized from diisopropyl ether to give 1-(4-chlorophenyl)-2-(2,4-dichlorophenyl)-5-hydroxymethyl-1H-imidazole-4-carboxylic acid. (1.56 g, 63% yield) as a pale brown solid, mp 138° C.; ¹H-NMR (200 MHz, CDCl₃): δ 3.05 (br s, 1H), 4.67 (s, 2H), 7.05–7.42 (m, 7H).

Part B: 1-(4-Chlorophenyl)-2-(2,4-dichlorophenyl)-5-hydroxymethyl-N-(piperidin-1-yl)-1H-imidazole-4-carboxamide. 1-(4-Chlorophenyl)-2-(2,4-dichlorophenyl)-5-hydroxymethyl-N-(piperidin-1-yl)-1H-imidazole-4-carboxamide was obtained from 1-(4-chlorophenyl)-2-(2,4-dichlorophenyl)-5-hydroxymethyl-1H-imidazole-4-carboxylic acid (0.78 g, 1.96 mmol), DIPEA (0.75 mL, 4.32 mmol), HBTU (0.89 g, 2.35 mmol) and 1-aminopiperidine (0.25 mL, 2.35 mmol) according to the procedure described herein above for 1-(4-chlorophenyl)-2-(2,4-dichlorophenyl)-5-fluoromethyl-N-(piperidin-1-yl)-1H-imidazole-4-carboxamide in 37% yield, mp 212–214° C.; ¹H-NMR (600 MHz, DMSO-d₆) δ 1.34–1.41 (m, 2H), 1.61–1.66 (m, 4H), 2.80–2.84 (m, 4H), 4.61–4.64 (m, 2H), 5.43–5.47 (m, 1H), 7.34 (d, J=8 Hz, 2H), 7.41–7.46 (m, 3H), 7.52 (d, J=2 Hz, 1H), 7.61 (d, J=8 Hz, 1H), 9.00 (s, 1H); ¹³C-NMR (150 MHz, DMSO-d₆) δ 23.29, 25.63, 52.57, 55.95, 127.53, 128.61, 129.13, 129.40, 129.58, 131.88, 133.78, 134.29, 134.69, 134.73, 135.88, 137.41, 142.66, 160.46; HRMS (C₂₂H₂₂Cl₃N₄O₂) [M+H]⁺: found m/z 479.0832, calcd 479.0808.

EXAMPLE 116

Synthesis of 1-(5-chloropyrid-2-yl)-2-(2-chlorophenyl)-5-ethyl-N-(piperidin-1-yl)-1H-imidazole-4-carboxamide

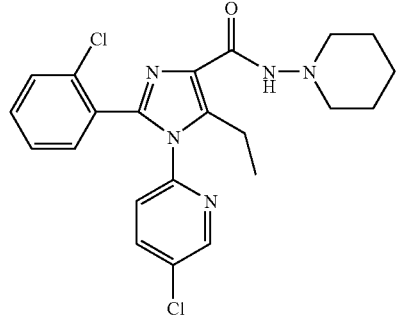

Part A: N-(5-chloropyrid-2-yl)-2-chlorobenzenecarboxamidine. To NaN(Si(CH₃)₃)₂ (500 mL, 1 M solution in THF) was added dropwise a solution of 5-chloro-2-aminopyridine (64.3 gram, 0.500 mol) in anhydrous THF (70 mL) while magnetically stirring under N₂. After the mixture was stirred for 20 minutes a solution of 2-chlorobenzonitrile (68.75 gram, 0.500 mol) in anhydrous THF (150 mL) was slowly added. The resulting mixture was stirred overnight, poured into ice-water (2 L) and extracted with dichloromethane, dried over Na₂SO₄ and concentrated in vacuo. Crystallisation from diisopropyl ether gave N-(5-chloropyrid-2-yl)-2-chlorobenzenecarboxamidine (109.87 gram, 82% yield); ¹H-NMR (200 MHz, CDCl₃) δ 5.95 (br s, 1H), 7.18 (d, J=8 Hz, 1H), 7.30–7.47 (m, 3H), 7.55–7.72 (m, 2H), 8.30 (d, J=2 Hz, 1H), 10.50 (br s, 1H).

Part B: Ethyl 1-(5-chloropyrid-2-yl)-2-(2-chlorophenyl)-5-ethyl-1H-imidazole-4-carboxylate. A mixture of N-(5-chloropyrid-2-yl)-2-chlorobenzenecarboxamidine (10.64 g, 0.04 mol), 3-bromo-2-oxovalerate (10.7 g, 0.048 mol) and NaHCO₃ (4.1 g, 0.048 mol) in ethanol (40 mL) was stirred at reflux temperature for 20 hours. Trifluoroacetic acid (TFA) (4.5 mL) was added and the resulting mixture was stirred at reflux temperature for 16 hours. After cooling to room temperature water and potassium carbonate were added to the mixture followed by extraction (3×) with ethyl acetate. The combined EtOAc layers were washed with H₂O (3×50 mL) and brine (3×50 mL). The organic layer was dried over $Na_2SO_4$ and concentrated in vacuo and further purified by column chromatography (ethyl acetate/petroleum ether=40/60 (v/v)) to yield ethyl 1-(5-chloropyrid-2-yl)-2-(2-chlorophenyl)-5-ethyl-1H-imidazole-4-carboxylate (7.23 g, 46% yield), $^1$H-NMR (200 MHz, CDCl$_3$) δ 1.10 (t, J=7 Hz, 3H), 1.40 (t, J=7 Hz, 3H), 3.05 (q, J=7 Hz, 2H), 4.32 (q, J=7 Hz, 2H), 7.00 (d, J=8 Hz, 1H), 7.20–7.30 (m, 3H), 7.43–7.51 (m, 1H), 7.60–7.68 (m, 1H), 8.48 (d, J=2 Hz, 1H).

Part C: 1-(5-Chloropyrid-2-yl)-2-(2-chlorophenyl)-5-ethyl-1H-imidazole-4-carboxylic acid. To a magnetically stirred solution of ethyl 1-(5-chloropyrid-2-yl)-2-(2-chlorophenyl)-5-ethyl-1H-imidazole-4-carboxylate (5.63 g, 0.0144 mol) in THF (50 mL) was added LiOH (0.700 g, 0.0288 mol) and $H_2O$ (50 mL). The resulting mixture was stirred at 60° C. for 16 hours to give a clear solution. After cooling to room temperature HCl (1 N solution, 30 mL) was added to give a precipitate which was collected by filtration, washed with water and dried in vacuo to give 1-(5-chloropyrid-2-yl)-2-(2-chlorophenyl)-5-ethyl-1H-imidazole-4-carboxylic acid (4.50 g, 86% yield). $^1$H-NMR (200 MHz, CDCl$_3$) δ 1.10 (t, J=7 Hz, 3H), 3.05 (q, J=7 Hz, 2H), 4.00 (br s, 1H), 7.00 (d, J=8 Hz, 1H), 7.22–7.32 (m, 3H), 7.37–7.45 (m, 1H), 7.62–7.70 (m, 1H), 8.48 (d, J=2 Hz, 1H).

Part D: 1-(5-chloropyrid-2-yl)-2-(2-chlorophenyl)-5-ethyl-N-(piperidin-1-yl)-1H-imidazole-4-carboxamide. To a magnetically stirred suspension of 1-(5-chloropyrid-2-yl)-2-(2-chlorophenyl)-5-ethyl-1H-imidazole-4-carboxylic acid (1.09 g, 3.00 mmol) in anhydrous $CH_3CN$ (25 mL) was successively added N,N-diisopropylethylamine (Hunig's base) (1.15 mL, 6.6 mmol), O-benzotriazol-1-yl-N,N,N',N'-tetramethyluronium hexafluorophosphate (HBTU) (1.36 g, 3.6 mmol) and 1-aminopiperidine (0.39 mL, 3.6 mmol). After stirring for 16 hours, the resulting mixture was concentrated in vacuo. The residue was dissolved in EtOAc, successively washed with aqueous $NaHCO_3$ solution, water and brine, dried over $Na_2SO_4$, filtered and concentrated to give a crude solid. This solid was further purified by flash chromatography (EtOAc/petroleum ether=65/35 (v/v)), followed by trituration with cyclohexane to give 1-(5-chloropyrid-2-yl)-2-(2-chlorophenyl)-5-ethyl-N-(piperidin-1-yl)-1H-imidazole-4-carboxamide (0.891 g, 66% yield), mp 217–219° C.

EXAMPLE 117

Synthesis of 1-(4-chlorophenyl)-2-(2,4-dichlorophenyl)-5-bromo-N-(piperidin-1-yl)-1H-imidazole-4-carboxamide

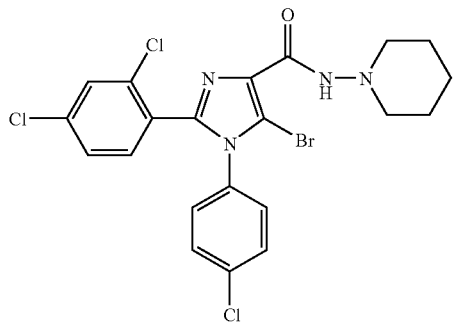

Part A: Tert-butyl 5-bromo-1-(4-chlorophenyl)-2-(2,4-dichlorophenyl)-1H-imidazole-4-carboxylate. To a cooled (−70° C.) and magnetically stirred solution of t-butyl 1-(4-chlorophenyl)-2-(2,4-dichlorophenyl)-1H-imidazole-4-carboxylate (4.24 g, 10.0 mmol) in anhydrous THF (80 mL) was added LDA (5.0 mL, 2 M solution in heptane/THF, 10.0 mmol) and the resulting mixture was stirred for 1 h under $N_2$. A solution of $(CBrF_2)_2$ (1.80 mL, 15.0 mmol) in anhydrous THF (20 mL) was added and the resulting solution was stirred at −70° C. for 1 h, allowed to attain room temperature and stirred for another 16 h. $NaHCO_3$ (5% aqueous solution) was added and extracted with $Et_2O$. The organic layer was washed with water, dried over $Na_2SO_4$, filtered, concentrated and further purified by column chromatography ($CH_2Cl_2$), Recrystallization from methyl tert-butyl ether (MTBE) gave tert-butyl 5-bromo-1-(4-chlorophenyl)-2-(2,4-dichlorophenyl)-1H-imidazole-4-carboxylate (4.30 g, 85% yield), mp 198–200° C. $^1$H-NMR (200 MHz, CDCl$_3$) δ 1.65 (s, 9H), 7.08 (br d, J=8 Hz, 2H), 7.25 (dd, J=8 and 2 Hz, 1H), 7.29 (d, J=2 Hz, 1H), 7.32–7.41 (m, 3H).

Part B: 5-Bromo-1-(4-chlorophenyl)-2-(2,4-dichlorophenyl)-1H-imidazole-4-carboxylic acid. To a magnetically stirred solution of tert-butyl 5-bromo-1-(4-chlorophenyl)-2-(2,4-dichlorophenyl)-1H-imidazole-4-carboxylate (4.30 g, 7.28 mmol) in $CH_2Cl_2$ (40 mL) was added excess TFA (10 mL). The solution was reacted at room temperature for 16 h, concentrated in vacuo and crystallized from diisopropyl ether to give 5-bromo-1-(4-chlorophenyl)-2-(2,4-dichlorophenyl)-1H-imidazole-4-carboxylic acid (2.69 g, 83% yield), mp 205–207° C.; $^1$H-NMR (200 MHz, CDCl$_3$) δ 6.50 (br s, 1H), 7.12 (br d, J=8 Hz, 2H), 7.23–7.45 (m, 5H).

Part C: 5-Bromo-1-(4-chlorophenyl)-2-(2,4-dichlorophenyl)-N-(piperidin-1-yl)-1H-imidazole-4-carboxamide. To a magnetically stirred suspension of 5-bromo-1-(4-chlorophenyl)-2-(2,4-dichlorophenyl)-1H-imidazole-4-carboxylic acid (1.34 g, 3.00 mmol) in anhydrous $CH_3CN$ (30 mL) was successively added N,N-diisopropylethylamine (Hunig's base) (1.15 mL, 6.6 mmol), O-benzotriazol-1-yl-N,N,N',N'-tetramethyluronium hexafluorophosphate (HBTU) (1.36 g, 3.6 mmol) and 1-aminopiperidine (0.39 mL, 3.6 mmol). After stirring for 16 h, the resulting precipitate was collected by filtration to give 5-bromo-1-(4-chlorophenyl)-2-(2,4-dichlorophenyl)-N-(piperidin-1-yl)-1H-imidazole-4-carboxamide (1.25 g, 79% yield). mp 181.5–183° C.; $^1$H-NMR (600 MHz, DMSO-d$_6$) δ 1.34–1.40 (m, 2H), 1.60–1.64 (m, 4H), 2.79–2.82 (m, 4H), 7.35 (d, J=8 Hz, 2H), 7.44 (dd, J=8 and 2 Hz, 1H), 7.48 (d, J=8 Hz, 2H), 7.55 (d, J=2 Hz, 1H), 7.66 (d, J=8 Hz, 1H), 8.90 (s, 1H); $^{13}$C-NMR (150 MHz, DMSO-d$_6$) δ 23.31, 25.67, 55.84, 109.28, 127.57, 128.27, 129.14, 129.58, 130.23, 132.23, 133.49, 134.66, 134.71, 134.98, 136.27, 144.18, 158.35; HRMS ($C_{21}H_{19}BrCl_3N_4O$) $[M+H]^+$: found m/z 526.9828, calcd 526.9808.

EXAMPLE 118

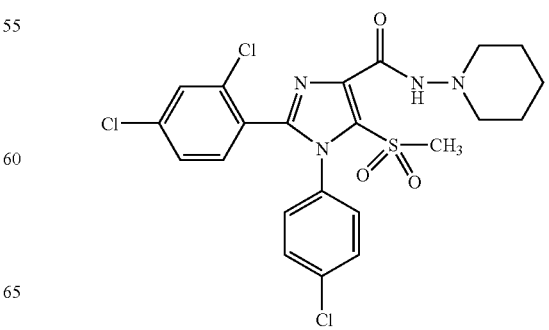

1-(4-Chlorophenyl)-2-(2,4-dichlorophenyl)-1H-imidazole-4-carboxylic acid

To a magnetically stirred solution of ethyl 1-(4-chlorophenyl)-2-(2,4-dichlorophenyl)-1H-imidazole-4-carboxylate (18.44 g, 0.0466 mol) in THF (240 ml) was added LiOH (2.24 g, 0.0932 mol) and H$_2$O (240 ml). The resulting mixture was stirred at 50° C. for 16 h to give a clear solution. After cooling to room temperature, HCl (1 N solution, 95 ml) and H$_2$O (240 ml) were added to give a precipitate which was collected by filtration, washed with water and dried in vacuo to give 1-(4-chlorophenyl)-2-(2,4-dichlorophenyl)-1H-imidazole-4-carboxylic acid (16.83 g, 98% yield), mp 138–142° C. (decomposition); $^1$H-NMR (600 MHz, DMSO-d$_6$) δ 7.08 (br d, J=8 Hz, 2H), 7.31–7.37 (m, 4H), 7.45 (d, J=8 Hz, 1H), 7.96 (s, 1H); $^{13}$C-NMR (150 MHz, DMSO-d$_6$) δ 126.87, 127.85, 127.91, 128.47, 129.36, 129.66, 133.56, 133.99, 134.44, 134.49, 135.54, 135.99, 143.77, 163.67.

Tert-butyl 1-(4-chlorophenyl)-2-(2,4-dichlorophenyl)-1H-imidazole-4-carboxylate To a magnetically stirred mixture of 1-(4-chlorophenyl)-2-(2,4-dichlorophenyl)-1H-imidazole-4-carboxylic acid (20.77 g, 0.0565 mol) and Boc$_2$O (24.63 g, 0.113 mol) in t-BuOH (275 ml) was added DMAP (2.07 g, 0.017 mol) and the resulting mixture was stirred for 16 h. After concentration in vacuo, toluene was added and the mixture was again concentrated. The residue was purified by column chromatography (CH$_2$Cl$_2$/acetone=95/5 (v/v)) and recrystallized from diisopropyl ether to give tert-butyl 1-(4-chlorophenyl)-2-(2,4-dichlorophenyl)-1H-imidazole-4-carboxylate (15.75 g, 66% yield), mp 178–180° C.; $^1$H-NMR (200 MHz, CDCl$_3$) δ 1.63 (s, 9H), 7.05 (br d, J=8 Hz, 2H), 7.25–7.37 (m, 4H), 7.52 (d, J=8 Hz, 1H), 7.80 (s, 1H).

Tert-butyl 1-(4-chlorophenyl)-2-(2,4-dichlorophenyl)-5-methylsulfanyl-1H-imidazole-4-carboxylate. To a cooled (−20° C.) and magnetically stirred solution of tert-butyl 1-(4-chlorophenyl)-2-(2,4-dichlorophenyl)-1H-imidazole-4-carboxylate (10.59 g, 25.0 mmol), in anhydrous THF (100 ml) was added LDA (15.0 ml, 2 M solution in heptane/THF, 30.0 mmol) and the resulting mixture was stirred for 1 hour under N$_2$. A solution of (CH$_3$S)$_2$ (2.7 ml, 30.0 mmol) in THF (20 ml) was added and the resulting solution was successively stirred at −40° C. for 1 h, allowed to attain room temperature and stirred for another 16 h. A saturated aqueous NH$_4$Cl solution (250 ml) was added and the resulting solution was extracted twice with ethyl acetate (EtOAc). The combined organic layers were washed with water, dried over MgSO$_4$, filtered and concentrated to give tert-butyl 1-(4-chlorophenyl)-2-(2,4-dichlorophenyl)-5-methylsulfanyl-1H-imidazole-4-carboxylate in 90% yield as an oil which slowly solidified; $^1$H-NMR (200 MHz, CDCl$_3$) δ 1.66 (s, 9H), 2.28 (s, 3H), 7.05 (br d, J~8 Hz, 2H), 7.25 (dd, J=8 and 2 Hz, 1H), 7.28 (d, J=2 Hz, 1H), 7.32–7.41 (m, 3H).

Tert-butyl 1-(4-chlorophenyl)-2-(2,4-dichlorophenyl)-5-methylsulfonyl-1H-imidazole-4-carboxylate. To a magnetically stirred solution of tert-butyl 1-(4-chlorophenyl)-2-(2,4-dichlorophenyl)-5-methylsulfanyl-1H-imidazole-4-carboxylate (6.00 g, 12.8 mmol) in CH$_2$Cl$_2$ (25 ml) was slowly added a solution of m-CPBA (6.90 g, 70% grade, 0.282 mol) in CH$_2$Cl$_2$ and the resulting mixture was stirred for 16 hours. The reaction mixture was twice washed with 2N NaOH solution and dried over Na$_2$SO$_4$, filtered and concentrated. The residue was purified by flash chromatography (Et$_2$O/petroleum ether=2/1 (v/v)) to give tert-butyl 1-(4-chlorophenyl)-2-(2,4-dichlorophenyl)-5-methylsulfonyl-1H-imidazole-4-carboxylate (4.76 g, 74% yield) as a white solid, mp 130° C.; $^1$H-NMR (400 MHz, CDCl$_3$) δ 1.66 (s, 9H), 3.34 (s, 3H), 7.15 (br d, J=8 Hz, 2H), 7.20–7.26 (m, 2H), 7.32–7.41 (m, 3H).

1-(4-Chlorophenyl)-2-(2,4-dichlorophenyl)-5-methylsulfonyl-1H-imidazole-4-carboxylic acid. To a magnetically stirred solution of tert-butyl 1-(4-chlorophenyl)-2-(2,4-dichlorophenyl)-5-methylsulfonyl-1H-imidazole-4-carboxylate (4.76 g, 9.49 mmol) in CH$_2$Cl$_2$ (60 ml) was added excess TFA (9.40 ml, 0.2124 mol) and Et$_3$SiH (3.8 ml, 0.0238 mol). The solution was reacted at room temperature for 16 h and concentrated in vacuo. Water was added and the formed precipitate was collected by filtration and subsequently dried to give 1-(4-chlorophenyl)-2-(2,4-dichlorophenyl)-5-methylsulfonyl-1H-imidazole-4-carboxylic acid in quantitative yield, mp~130° C. (dec); $^1$H-NMR (400 MHz, CDCl$_3$) δ 3.45 (s, 3H), 3.50 (br s, 1H), 7.40 (br d, J~8 Hz, 2H), 7.42 (dd, J=8 and 2 Hz, 1H), 7.50 (br d, J~8 Hz, 2H), 7.59 (d, J=2 Hz, 1H), 7.61 (d, J=8 Hz, 1H).

1-(4-Chlorophenyl)-2-(2,4-dichlorophenyl)-5-methylsulfonyl-N-(piperidin-1-yl)-1H-imidazole-4-carboxamide.

To a magnetically stirred suspension of 1-(4-chlorophenyl)-2-(2,4-dichlorophenyl)-5-methylsulfonyl-1H-imidazole-4-carboxylic acid (2.23 g, 5.01 mmol) in anhydrous CH$_3$CN (50 ml) was successively added N,N-diisopropylethylamine (Hunig's base) (1.90 ml, 11.0 mmol), O-benzotriazol-1-yl-N,N,N',N'-tetramethyluronium hexafluorophosphate (HBTU) (2.27 g, 5.99 mmol) and 1-aminopiperidine (0.65 ml, 6.03 mmol). After stirring for 16 h, the resulting mixture was concentrated in vacuo. The residue was dissolved in EtOAc, successively washed with aqueous NaHCO$_3$ solution, water and brine, dried over Na$_2$SO$_4$, filtered and concentrated to give a crude solid. This solid was further purified by flash chromatography (silicagel, EtOAc) and triturated with methyl-tert-butyl ether to give 1-(4-chlorophenyl)-2-(2,4-dichlorophenyl)-5-methylsulfonyl-N-(piperidin-1-yl)-1H-imidazole-4-carboxamide in 84% yield, mp 181–185° C. (dec); $^1$H-NMR (600 MHz, DMSO-d$_6$) δ 1.35–1.41 (m, 2H), 1.61–1.66 (m, 4H), 2.80–2.84 (m, 4H), 3.52 (s, 3H), 7.38 (d, J=8 Hz, 2H), 7.42 (dd, J=8 and 2 Hz, 1H), 7.46 (d, J=8 Hz, 2H), 7.57 (d, J=2 Hz, 1H), 7.62 (d, J=8 Hz, 1H), 9.40 (s, 1H); HRMS (C$_{22}$H$_{22}$Cl$_3$N$_4$O$_3$S) [M+H]$^+$: found m/z 527.0469, calcd 527.0478.

EXAMPLE 119

Analogously was prepared: 1-(4-chlorophenyl)-2-(2,4-dichlorophenyl)-5-methylsulfonyl-N-(cyclohexyl)-1H-imidazole-4-carboxamide. Melting point: 191–192° C.

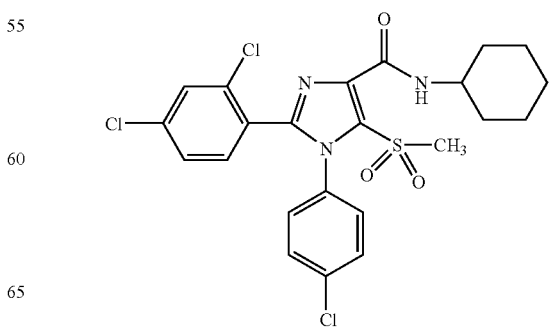

EXAMPLE 120

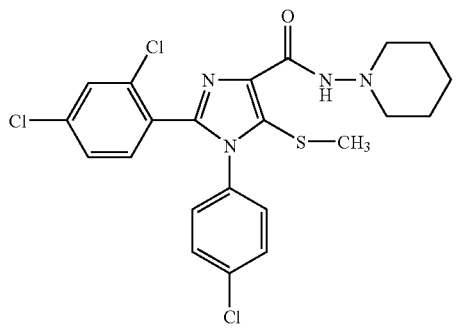

1-(4-Chlorophenyl)-2-(2,4-dichlorophenyl)-5-methylsulfanyl-1H-imidazole-4-carboxylic acid. To a magnetically stirred solution of tert-butyl 1-(4-chlorophenyl)-2-(2,4-dichlorophenyl)-5-methylsulfanyl-1H-imidazole-4-carboxylate (4.00 g, 8.53 mmol) in $CH_2Cl_2$ (60 ml) was added excess TFA (8.40 ml, 0.111 mol). The solution was reacted at room temperature for 16 hours and subsequently concentrated in vacuo. Water was added and the formed precipitate was collected by filtration and subsequently dried to give 1-(4-chlorophenyl)-2-(2,4-dichlorophenyl)-5-methylsulfanyl-1H-imidazole-4-carboxylic acid in 98% yield, mp~100° C. (decomposition); $^1$H-NMR (400 MHz, $CDCl_3$) δ 2.41 (s, 3H), 3.60 (br s, 1H), 7.08 (br d, J~8 Hz, 2H), 7.26 (dd, J=8 and 2 Hz, 1H), 7.30 (d, J=8 Hz, 1H), 7.35 (d, J=2 Hz, 1H), 7.37 (br d, J~8 Hz, 2H).

1-(4-Chlorophenyl)-2-(2,4-dichlorophenyl)-5-methylsulfanyl-N-(piperidin-1-yl)-1H-imidazole-4-carboxamide. To a magnetically stirred suspension of 1-(4-chlorophenyl)-2-(2,4-dichlorophenyl)-5-methylsulfanyl-1H-imidazole-4-carboxylic acid (1.72 g, 4.16 mmol) in anhydrous $CH_3CN$ (45 ml) was successively added N,N-diisopropylethylamine (Hunig's base) (1.60 ml, 9.20 mmol), O-benzotriazol-1-yl-N,N,N',N'-tetramethyluronium hexafluorophosphate (HBTU) (1.89 g, 4.99 mmol) and 1-aminopiperidine (0.54 ml, 5.01 mmol). After stirring for 40 h, water was added and the resulting mixture was extracted with dichloromethane. the dichloromethane layer was successively twice washed with an 1N HCl solution and water, dried over $MgSO_4$, filtered and concentrated to give a crude oil. This oil was further purified by flash chromatography (silicagel, EtOAc) and triturated with diethyl ether to give 1-(4-chlorophenyl)-2-(2,4-dichlorophenyl)-5-methylsulfanyl-N-(piperidin-1-yl)-1H-imidazole-4-carboxamide in 72% yield, mp 170° C. (dec); $^1$H-NMR (600 MHz, DMSO-$d_6$) δ 1.35–1.42 (m, 2H), 1.62–1.67 (m, 4H), 2.35 (s, 3H), 2.80–2.84 (m, 4H), 7.29 (d, J=8 Hz, 2H), 7.42 (dd, J=8 and 2 Hz, 1H), 7.45 (d, J=8 Hz, 2H), 7.52 (d, J=2 Hz, 1H), 7.62 (d, J=8 Hz, 1H), 8.90 (s, 1H); $^{13}$C-NMR (150 MHz, DMSO-$d_6$) δ 19.26, 23.32, 25.63, 55.98, 127.52, 128.61, 129.14, 129.23, 129.86, 130.12, 130.18, 133.86, 134.45, 134.66, 136.01, 137.12, 144.04, 158.98; HRMS ($C_{22}H_{22}Cl_3N_4OS$) [M+H]$^+$: found m/z 495.0592, calcd 495.0580.

EXAMPLE 121

Analogously was prepared: 1-(4-chlorophenyl)-2-(2,4-dichlorophenyl)-5-methylsulfanyl-N-(cyclohexyl)-1H-imidazole-4-carboxamide. Melting point: 152–154° C.

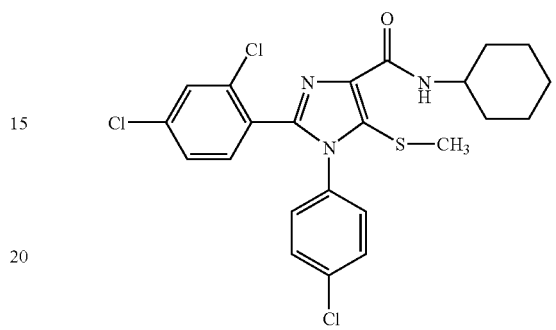

The affinity of the compounds of the invention for cannabinoid $CB_1$ receptors was determined using membrane preparations of Chinese hamster ovary (CHO) cells in which the human cannabinoid $CB_1$ receptor was stably transfected in conjunction with [$^3$H]CP-55,940 as radioligand. After incubation of a freshly prepared cell membrane preparation with the [$^3$H]-ligand, with or without addition of compounds of the invention, separation of bound and free ligand was performed by filtration over glassfiber filters. Radioactivity on the filter was measured by liquid scintillation counting.

The cannabinoid $CB_1$ antagonistic activity of compounds of the invention was determined by functional studies using CHO cells in which human cannabinoid $CB_1$ receptors were stably expressed. Adenylyl cyclase was stimulated using forskolin and measured by quantifying the amount of accumulated cyclic AMP. Concomitant activation of $CB_1$ receptors by $CB_1$ receptor agonists (e.g. CP-55,940 or (R)-WIN-55,212–2) can attenuate the forskolin-induced accumulation of cAMP in a concentration-dependent manner. This $CB_1$ receptor-mediated response can be antagonized by $CB_1$ receptor antagonists such as the compounds of the invention.

Cannabinoid agonistic of partial agonistic activity of compounds of the invention can be determined according to published methods, such as assessment of in vivo cannabimimetic effects (Wiley, J. L. et al., *J. Pharmacol. Exp. Ther.* 2001, 296, 1013).

Affinities and antagonistic activity of some compounds disclosed herein are reported in Table 1.

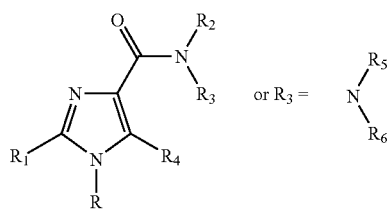

| | | | | | | hCB$_1$ | |
|---|---|---|---|---|---|---|---|
| Ex | R | R$_1$ | R$_2$ | R$_3$ | R$_4$ | pK$_i$ | pA$_2$ |
| 96 | phenyl | 2,5-diCl-phenyl | H | cyclohexyl | CH$_3$ | 8.2 | |
| 100 | phenyl | 2,5-diCl-phenyl | H | cyclohexyl | ethyl | | |

-continued

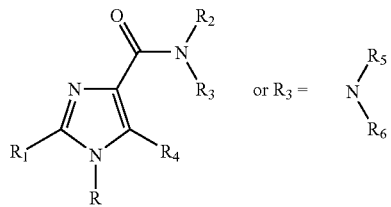

| Ex | R | R₁ | R₂ | R₃ | R₄ | hCB₁ pK$_i$ | pA$_2$ |
|---|---|---|---|---|---|---|---|
| 95 | phenyl | 2,5-diCl-phenyl | H | piperidin-1-yl | CH₃ | 7.2 | |
| 101 | phenyl | 2,5-diCl-phenyl | H | piperidin-1-yl | ethyl | | |
| 99 | phenyl | 1,5-diMe-1H-pyrrol-2-yl | H | cyclohexyl | ethyl | | |
| 73 | 3-fluorophenyl | 2-Cl-phenyl | H | cyclohexyl | CH₃ | 7.9 | |
| 71 | 3-fluorophenyl | 2-Cl-phenyl | H | piperidin-1-yl | CH₃ | 7.4 | |
| 74 | 3-fluorophenyl | 2-Cl-phenyl | H | 2-(4-F-phenyl)ethyl | CH₃ | 6.4 | |
| 32 | 4-fluorophenyl | 2,4-dichlorophenyl | H | cyclohexyl | H | 7.6 | |
| 64 | 4-fluorophenyl | 2,4-dichlorophenyl | H | cyclohexyl | CH₃ | | |
| 31 | 4-fluorophenyl | 2,4-dichlorophenyl | H | piperidin-1-yl | H | 6.7 | |
| 62 | 4-fluorophenyl | 2,4-dichlorophenyl | H | piperidin-1-yl | CH₃ | 7.5 | 7.7 |
| 21 | 4-bromophenyl | 2,4-dichlorophenyl | H | n-pentyl | ethyl | 7.5 | >9.0 |
| 23 | 4-bromophenyl | 2,4-dichlorophenyl | H | O-tert-butyl | H | 6.4 | 9.0 |
| 16 | 4-bromophenyl | 2,4-dichlorophenyl | H | O-tert-butyl | CH₃ | 6.2 | 7.8 |
| 18 | 4-bromophenyl | 2,4-dichlorophenyl | H | O-tert-butyl | ethyl | | |
| 20 | 4-bromophenyl | 2,4-dichlorophenyl | H | cyclohexyl | ethyl | 7.0 | >9.0 |
| 24 | 4-bromophenyl | 2,4-dichlorophenyl | H | pyrrolidin-1-yl | H | | |
| 22 | 4-bromophenyl | 2,4-dichlorophenyl | H | piperidin-1-yl | H | 6.4 | 8.0 |
| 109 | 4-bromophenyl | 2,4-dichlorophenyl | H | piperidin-1-yl | Cl | 6.6 | 8.8 |
| 17 | 4-bromophenyl | 2,4-dichlorophenyl | H | piperidin-1-yl | CH₃ | 7.3 | 8.8 |
| 19 | 4-bromophenyl | 2,4-dichlorophenyl | H | piperidin-1-yl | ethyl | 7.5 | 8.9 |
| 25 | 4-bromophenyl | 2,4-dichlorophenyl | H | Azepan-1-yl | H | 6.9 | 8.0 |
| 69 | 4-chlorophenyl | 1,5-diMe-1H-pyrrol-2-yl | H | cyclohexyl | CH₃ | 7.4 | |
| 70 | 4-chlorophenyl | 1,5-diMe-1H-pyrrol-2-yl | H | piperidin-1-yl | CH₃ | 8.3 | |
| 103 | 4-chlorophenyl | 3-Me-pyridin-2-yl | H | cyclohexyl | CH₃ | | |
| 102 | 4-chlorophenyl | 3-Me-pyridin-2-yl | H | piperidin-1-yl | CH₃ | | |
| 33 | 4-chlorophenyl | 2-fluoro-4-chlorophenyl | H | cyclohexyl | H | 6.3 | |
| 68 | 4-chlorophenyl | 2-fluoro-4-chlorophenyl | H | cyclohexyl | CH₃ | 6.7 | |
| 67 | 4-chlorophenyl | 2-fluoro-4-chlorophenyl | H | n-pentyl | CH₃ | 6.4 | |
| 30 | 4-chlorophenyl | 2-fluoro-4-chlorophenyl | H | piperidin-1-yl | H | 7.6 | |
| 66 | 4-chlorophenyl | 2-fluoro-4-chlorophenyl | H | piperidin-1-yl | CH₃ | 6.3 | |
| 50 | 4-chlorophenyl | 2,4-dichlorophenyl | CH₃ | methyl | CH₃ | 8.3 | |
| 37 | 4-chlorophenyl | 2,4-dichlorophenyl | ethyl | ethyl | H | | |
| 85 | 4-chlorophenyl | 2,4-dichlorophenyl | H | 2-fluoroethyl | CH₃ | 7.6 | |
| 4 | 4-chlorophenyl | 2,4-dichlorophenyl | H | phenyl | H | 6.9 | |
| 82 | 4-chlorophenyl | 2,4-dichlorophenyl | H | phenyl | CH₃ | 8.6 | |
| 104 | 4-chlorophenyl | 2,4-dichlorophenyl | H | 3-CF₃-phenyl | CH₃ | 8.2 | |
| 6 | 4-chlorophenyl | 2,4-dichlorophenyl | CH₃ | benzyl | H | 7.2 | 7.3 |
| 105 | 4-chlorophenyl | 2,4-dichlorophenyl | H | 3-CF₃-benzyl | CH₃ | 7.5 | |
| 106 | 4-chlorophenyl | 2,4-dichlorophenyl | H | 4-CF₃-benzyl | CH₃ | 7.0 | 8.9 |
| 27 | 4-chlorophenyl | 2,4-dichlorophenyl | H | 4-fluorobenzyl | H | 7.2 | 8.4 |
| 90 | 4-chlorophenyl | 2,4-dichlorophenyl | H | 4-fluorobenzyl | CH₃ | 8.0 | |
| 108 | 4-chlorophenyl | 2,4-dichlorophenyl | H | cycloheptyl | CH₃ | 8.1 | 9.1 |
| 107 | 4-chlorophenyl | 2,4-dichlorophenyl | H | cyclopentyl | CH₃ | 6.8 | 8.9 |
| 119 | 4-chlorophenyl | 2,4-dichlorophenyl | H | cyclohexyl | SO₂CH₃ | 7.2 | |
| 121 | 4-chlorophenyl | 2,4-dichlorophenyl | H | cyclohexyl | SCH₃ | 7.2 | |
| 5 | 4-chlorophenyl | 2,4-dichlorophenyl | H | cyclohexyl | H | 7.1 | 8.1 |
| 113 | 4-chlorophenyl | 2,4-dichlorophenyl | H | cyclohexyl | cyano | 7.8 | |
| 112 | 4-chlorophenyl | 2,4-dichlorophenyl | H | cyclohexyl | iodo | 8.2 | |
| 86 | 4-chlorophenyl | 2,4-dichlorophenyl | H | 4-OH-cyclohexyl | CH₃ | 6.9 | 7.8 |
| 108 | 4-chlorophenyl | 2,4-dichlorophenyl | H | cycloheptyl | CH₃ | 8.1 | 9.1 |
| 92 | 4-chlorophenyl | 2,4-dichlorophenyl | H | 1-azepanyl | CH₃ | 7.2 | 8.8 |
| 89 | 4-chlorophenyl | 2,4-dichlorophenyl | H | endo-bicyclo [2.2.1]hept-2-yl | CH₃ | 8.2 | |
| 84 | 4-chlorophenyl | 2,4-dichlorophenyl | H | exo-bicyclo [2.2.1]hept-2-yl | CH₃ | 7.8 | 8.9 |
| 94 | 4-chlorophenyl | 2,4-dichlorophenyl | H | morpholin-4-yl | CH₃ | 7.0 | 7.5 |
| 91 | 4-chlorophenyl | 2,4-dichlorophenyl | H | n-pentyl | CH₃ | 7.5 | |
| 3 | 4-chlorophenyl | 2,4-dichlorophenyl | H | O-tert-butyl | H | 6.8 | 7.5 |
| 13 | 4-chlorophenyl | 2,4-dichlorophenyl | H | O-tert-butyl | CH₃ | 7.1 | 8.5 |
| 14 | 4-chlorophenyl | 2,4-dichlorophenyl | H | O-tert-butyl | ethyl | 7.0 | 9.9 |
| 1 | 4-chlorophenyl | 2,4-dichlorophenyl | H | piperidin-1-yl | H | 7.9 | 8.2 |
| 12 | 4-chlorophenyl | 2,4-dichlorophenyl | H | piperidin-1-yl | CH₃ | 7.9 | 8.9 |
| 114 | 4-chlorophenyl | 2,4-dichlorophenyl | H | piperidin-1-yl | CH₂F | 7.2 | |
| 115 | 4-chlorophenyl | 2,4-dichlorophenyl | H | piperidin-1-yl | CH₂OH | 7.5 | |
| 15 | 4-chlorophenyl | 2,4-dichlorophenyl | H | piperidin-1-yl | ethyl | 8.0 | 9.3 |
| 110 | 4-chlorophenyl | 2,4-dichlorophenyl | H | piperidin-1-yl | cyano | 7.5 | 8.6 |
| 111 | 4-chlorophenyl | 2,4-dichlorophenyl | H | piperidin-1-yl | iodo | 8.2 | 8.6 |

-continued

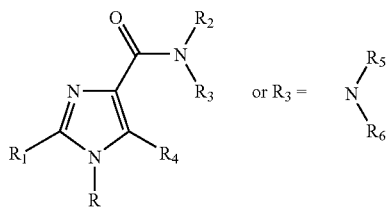

*including the nitrogen atom to which $R_2$ and $R_3$ are attached in the general formula.

| | | | | | | hCB$_1$ | |
|---|---|---|---|---|---|---|---|
| Ex | R | R$_1$ | R$_2$ | R$_3$ | R$_4$ | pK$_i$ | pA$_2$ |
| 117 | 4-chlorophenyl | 2,4-dichlorophenyl | H | piperidin-1-yl | bromo | 8.0 | 8.6 |
| 118 | 4-chlorophenyl | 2,4-dichlorophenyl | H | piperidin-1-yl | SO$_2$CH$_3$ | 7.8 | 8.5 |
| 120 | 4-chlorophenyl | 2,4-dichlorophenyl | H | piperidin-1-yl | SCH$_3$ | 7.9 | 9.2 |
| 2 | 4-chlorophenyl | 2,4-dichlorophenyl | H | pyrrolidin-1-yl | H | 7.0 | 7.6 |
| 93 | 4-chlorophenyl | 2,4-dichlorophenyl | H | pyrrolidin-1-yl | CH$_3$ | 7.7 | 8.2 |
| 83 | 4-chlorophenyl | 2,4-dichlorophenyl | H | Tetrahydro-2H-pyran-2-yloxy- | CH$_3$ | 8.4 | |
| 26 | 4-chlorophenyl | 2,4-dichlorophenyl | H | (octahydrocyclopenta[c]pyrrol-2-yl) | H | 6.3 | 8.0 |
| 81 | 4-chlorophenyl | 2,4-dichlorophenyl | H | | CH$_3$ | 7.5 | 9.8 |
| 7 | 4-chlorophenyl | 2,4-dichlorophenyl | hexahydro-azepin-1-yl* | | H | | |
| 87 | 4-chlorophenyl | 2,4-dichlorophenyl | 4-hydroxypiperidin-1-yl* | | CH$_3$ | 6.8 | |
| 88 | 4-chlorophenyl | 2,4-dichlorophenyl | 1,2,3,4-tetrahydroisoquinolin-1-yl* | | CH$_3$ | 8.0 | 8.4 |
| 40 | 4-chlorophenyl | 2-CF$_3$-4-chlorophenyl | H | 1-adamantyl | H | | |
| 41 | 4-chlorophenyl | 2-CF$_3$-4-chlorophenyl | H | 2,2,2-trifluoroethyl | H | | |
| 65 | 4-chlorophenyl | 2-CF$_3$-4-chlorophenyl | H | n-pentyl | CH$_3$ | | |
| 38 | 4-chlorophenyl | 2-CF$_3$-4-chlorophenyl | H | cyclohexyl | H | 6.7 | 7.7 |
| 57 | 4-chlorophenyl | 2-CF$_3$-4-chlorophenyl | H | cyclohexyl | CH$_3$ | | |
| 39 | 4-chlorophenyl | 2-CF$_3$-4-chlorophenyl | H | piperidin-1-yl | H | 6.5 | 7.3 |
| 58 | 4-chlorophenyl | 2-CF$_3$-4-chlorophenyl | H | piperidin-1-yl | CH$_3$ | 6.7 | |
| 29 | 4-chlorophenyl | 2-OCH$_3$-4-Cl-phenyl | H | cyclohexyl | H | 6.4 | 7.0 |
| 61 | 4-chlorophenyl | 2-OCH$_3$-4-Cl-phenyl | H | cyclohexyl | CH$_3$ | | |
| 34 | 4-chlorophenyl | 2-OCH$_3$-4-Cl-phenyl | H | n-pentyl | H | | |
| 59 | 4-chlorophenyl | 2-OCH$_3$-4-Cl-phenyl | H | n-pentyl | CH$_3$ | 6.3 | |
| 28 | 4-chlorophenyl | 2-OCH$_3$-4-Cl-phenyl | H | piperidin-1-yl | H | 7.2 | |
| 60 | 4-chlorophenyl | 2-OCH$_3$-4-Cl-phenyl | H | piperidin-1-yl | CH$_3$ | | |
| 48 | 4-CF$_3$-phenyl | 2,4-dichlorophenyl | H | cyclohexyl | H | 6.5 | 9.6 |
| 47 | 4-CF$_3$-phenyl | 2,4-dichlorophenyl | H | cyclohexyl | CH$_3$ | 6.8 | |
| 46 | 4-CF$_3$-phenyl | 2,4-dichlorophenyl | H | piperidin-1-yl | H | 7.3 | 8.2 |
| 45 | 4-CF$_3$-phenyl | 2,4-dichlorophenyl | H | piperidin-1-yl | CH$_3$ | 7.8 | 8.8 |
| 36 | 4-OCH$_3$-phenyl | 2,4-dichlorophenyl | H | cyclohexyl | H | 6.8 | 8.2 |
| 49 | 4-OCH$_3$-phenyl | 2,4-dichlorophenyl | H | cyclohexyl | CH$_3$ | 6.9 | |
| 35 | 4-OCH$_3$-phenyl | 2,4-dichlorophenyl | H | piperidin-1-yl | H | 7.3 | |
| 63 | 4-OCH$_3$-phenyl | 2,4-dichlorophenyl | H | piperidin-1-yl | CH$_3$ | 7.1 | 9.0 |
| 97 | 2,5-diF-phenyl | 2,4-dichlorophenyl | H | cyclohexyl | CH$_3$ | 7.3 | |
| 98 | 2,5-diF-phenyl | 2,4-dichlorophenyl | H | cyclohexyl | ethyl | 7.8 | |
| 9 | 2,4-diCl-phenyl | 4-chlorophenyl | H | O-tert-butyl | H | 6.2 | |
| 11 | 2,4-diCl-phenyl | 4-chlorophenyl | H | O-tert-butyl | CH$_3$ | 6.3 | |
| 8 | 2,4-diCl-phenyl | 4-chlorophenyl | H | piperidin-1-yl | H | | |
| 10 | 2,4-diCl-phenyl | 4-chlorophenyl | H | piperidin-1-yl | CH$_3$ | 6.5 | 8.1 |
| 44 | pyridin-3-yl | 2,4-dichlorophenyl | H | n-pentyl | H | | |
| 43 | pyridin-3-yl | 2,4-dichlorophenyl | H | cyclohexyl | H | | |
| 42 | pyridin-3-yl | 2,4-dichlorophenyl | H | piperidin-1-yl | H | 6.2 | |
| 116 | 5-Cl-pyridin-2-yl | 2-chlorophenyl | H | piperidin-1-yl | ethyl | 7.9 | |
| 55 | 5-Cl-pyridin-2-yl | 2,4-dichlorophenyl | H | n-pentyl | CH$_3$ | 7.3 | |
| 79 | 5-Cl-pyridin-2-yl | 2,4-dichlorophenyl | H | n-pentyl | ethyl | 7.8 | |
| 54 | 5-Cl-pyridin-2-yl | 2,4-dichlorophenyl | H | cyclohexyl | CH$_3$ | 7.0 | |
| 78 | 5-Cl-pyridin-2-yl | 2,4-dichlorophenyl | H | cyclohexyl | ethyl | 8.5 | |
| 51 | 5-Cl-pyridin-2-yl | 2,4-dichlorophenyl | H | piperidin-1-yl | CH$_3$ | 7.3 | 8.7 |
| 75 | 5-Cl-pyridin-2-yl | 2,4-dichlorophenyl | H | piperidin-1-yl | ethyl | 7.0 | |
| 52 | 5-Cl-pyridin-2-yl | 2,4-dichlorophenyl | H | morpholin-4-yl | CH$_3$ | 6.3 | 8.6 |
| 76 | 5-Cl-pyridin-2-yl | 2,4-dichlorophenyl | H | morpholin-4-yl | ethyl | 6.6 | |
| 56 | 5-Cl-pyridin-2-yl | 2,4-dichlorophenyl | H | 4-fluorobenzyl | CH$_3$ | 6.8 | |
| 80 | 5-Cl-pyridin-2-yl | 2,4-dichlorophenyl | H | 2-(4-F-phenyl)ethyl | ethyl | 6.5 | |
| 53 | 5-Cl-pyridin-2-yl | 2,4-dichlorophenyl | H | 1-azepanyl | CH$_3$ | 7.3 | |
| 77 | 5-Cl-pyridin-2-yl | 2,4-dichlorophenyl | H | 1-azepanyl | ethyl | 7.5 | |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A compound of the formula:

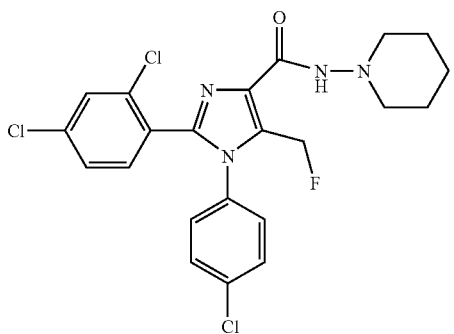

an enantiomer or a prodrug thereof, or a pharmaceutically acceptable salt of any of the foregoing.

2. A compound of the formula:

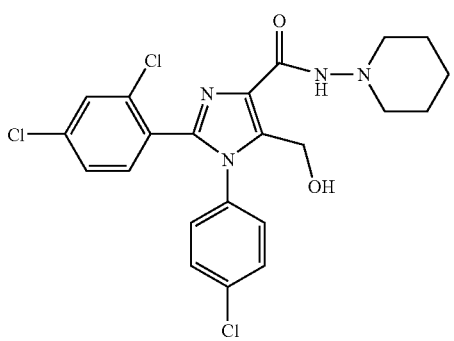

an enantiomer or a prodrug thereof, or a pharmaceutically acceptable salt of any of the foregoing.

3. A compound of the formula:

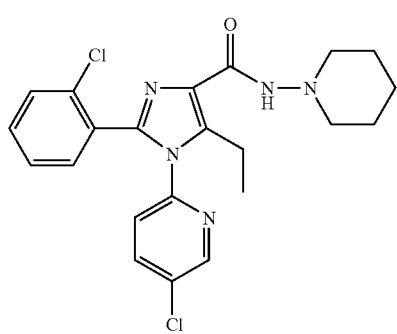

an enantiomer or a prodrug thereof, or a pharmaceutically acceptable salt of any of the foregoing.

4. A compound of the formula:

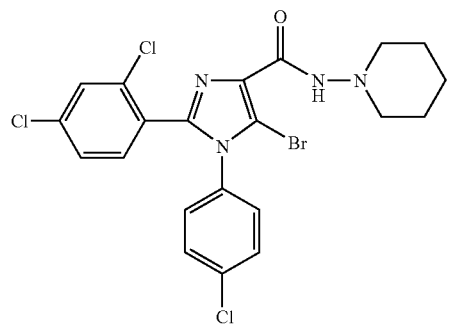

an enantiomer or a prodrug thereof, or a pharmaceutically acceptable salt of any of the foregoing.

5. A composition comprising:
   (a) an amount of the compound as claimed in claim 1, an enantiomer thereof, a prodrug thereof, or a pharmaceutically acceptable salt of any of the foregoing, or a combination of two or more of the foregoing, and
   (b) at least one auxiliary substance.

6. A composition comprising:
   (a) an amount of the compound as claimed in claim 2, an enantiomer thereof, a prodrug thereof, or a pharmaceutically acceptable salt of any of the foregoing, or a combination of two or more of the foregoing, and
   (b) at least one auxiliary substance.

7. A composition comprising:
   (a) an amount of the compound as claimed in claim 3, an enantiomer thereof, a prodrug thereof, or a pharmaceutically acceptable salt of any of the foregoing, or a combination of two or more of the foregoing, and
   (b) at least one auxiliary substance.

8. A composition comprising:
   (a) an amount of the compound as claimed in claim 4, an enantiomer thereof, a prodrug thereof, or a pharmaceutically acceptable salt of any of the foregoing, or a combination of two or more of the foregoing, and
   (b) at least one auxiliary substance.

9. The composition of one of claims 5, 6, 7, and 8, wherein the amount is an amount effective for treating at least one disorder involving cannabinoid neurotransmission wherein the cannabinoid neurotransmission disorder is selected from the group consisting of psychosis, anxiety, depression, attention deficits, memory disorders, cognitive disorders, appetite disorders, obesity, addition, appetence, drug dependence, dementia, dystonia, muscle spasticity, tremor, epilepsy, multiple sclerosis, traumatic brain injury, stroke, Parkinson's disease, Alzheimer's disease, epilepsy, Huntington's disease, Tourette's Syndrome, cerebral ischaemia, cerebral apoplexy, craniocerebral trauma, spinal cord injury, plaque sclerosis, viral encephalitis, pain, septic shock, glaucoma, diabetes, emesis, nausea, asthma, gastric ulcers, and diarrhea.

10. A method of treating at least one disorder involving cannabinoid neurotransmission wherein the cannabinoid neurotransmission disorder is selected from the group consisting of psychosis, anxiety, depression, attention deficits, memory disorders, cognitive disorders, appetite disorders, obesity, addiction, appetence, drug dependence, dementia, dystonia, muscle spasticity, tremor, epilepsy, multiple sclerosis, traumatic brain injury, stroke, Parkinson's disease, Alzheimer's disease, epilepsy, Huntington's disease, Tourette's Syndrome, cerebral ischaemia, cerebral apoplexy, craniocerebral trauma, spinal cord injury, plaque sclerosis, viral encephalitis, pain, septic shock, glaucoma, diabetes, emesis, nausea, asthma, gastric ulcers, and diarrhea in a human or animal patient in need of such treating, comprising administering to the patient an amount effective for the treating of a compound as claimed in claim 1, an enantiomer thereof, a prodrug thereof, or a pharmaceutically acceptable salt of any of the foregoing, or a combination of two or more of the foregoing.

11. A method of treating at least one disorder involving cannabinoid neurotransmission wherein the cannabinoid neurotransmission disorder is selected from the group consisting of psychosis, anxiety, depression, attention deficits, memory disorders, cognitive disorders, appetite disorders, obesity, addition, appetence, drug dependence, dementia, dystonia, muscle spasticity, tremor, epilepsy, multiple sclerosis, traumatic brain injury, stroke, Parkinson's disease, Alzheimer's disease, epilepsy, Huntington's disease, Tourette's Syndrome, cerebral ischaemia, cerebral apoplexy, craniocerebral trauma, spinal cord injury, plaque sclerosis, viral encephalitis, pain, septic shock, glaucoma, diabetes, emesis, nausea, asthma, gastric ulcers, and diarrhea in a human or animal patient in need of such treating, comprising administering to the patient an amount effective for the treating of a compound as claimed in claim 2, an enantiomer thereof, a prodrug thereof, or a pharmaceutically acceptable salt of any of the foregoing, or a combination of two or more of the foregoing.

12. A method of treating at least one disorder involving cannabinoid neurotransmission wherein the cannabinoid neurotransmission disorder is selected from the group consisting of psychosis, anxiety, depression, attention deficits, memory disorders, cognitive disorders, appetite disorders, obesity, addition, appetence, drug dependence, dementia, dystonia, muscle spasticity, tremor, epilepsy, multiple sclerosis, traumatic brain injury, stroke, Parkinson's disease, Alzheimer's disease, epilepsy, Huntington's disease, Tourette's Syndrome, cerebral ischaemia, cerebral apoplexy, craniocerebral trauma, spinal cord injury, plaque sclerosis, viral encephalitis, pain, septic shock, glaucoma, diabetes, emesis, nausea, asthma, gastric ulcers, and diarrhea in a human or animal patient in need of such treating, comprising administering to the patient an amount effective for the treating of a compound as claimed in claim 3, an enantiomer thereof, a prodrug thereof, or a pharmaceutically acceptable salt of any of the foregoing, or a combination of two or more of the foregoing.

13. A method of treating at least one disorder involving cannabinoid neurotransmission wherein the cannabinoid neurotransmission disorder is selected from the group consisting of psychosis, anxiety, depression, attention deficits, memory disorders, cognitive disorders, appetite disorders, obesity, addition, appetence, drug dependence, dementia, dystonia, muscle spasticity, tremor, epilepsy, multiple sclerosis, traumatic brain injury, stroke, Parkinson's disease, Alzheimer's disease, epilepsy, Huntington's disease, Tourette's Syndrome, cerebral ischaemia, cerebral apoplexy, craniocerebral trauma, spinal cord injury, plaque sclerosis, viral encephalitis, pain, septic shock, glaucoma, diabetes, emesis, nausea, asthma, gastric ulcers, and diarrhea in a human or animal patient in need of such treating, comprising administering to the patient an amount effective for the treating of a compound as claimed in claim 4, an enantiomer thereof, a prodrug thereof, or a pharmaceutically acceptable salt of any of the foregoing, or a combination of two or more of the foregoing.

\* \* \* \* \*